United States Patent
Zalevsky et al.

(10) Patent No.: US 11,202,040 B2
(45) Date of Patent: Dec. 14, 2021

(54) SYSTEM AND METHOD FOR MONITORING A SAMPLE

(71) Applicant: CONTINUSE BIOMETRICS LTD., Tel Aviv (IL)

(72) Inventors: Zeev Zalevsky, Rosh HaAyin (IL); Ran Califa, Givataym (IL); Mark Golberg, Rehovot (IL); Zeev Markman, Bet-Dagan (IL); Michael Shegei, Petah-Tikva (IL); Yevgeny Beiderman, Tel Aviv (IL)

(73) Assignee: CONTINUSE BIOMETRICS LTD., Tel Aviv (IL)

( * ) Notice: Subject to any disclaimer, the term of this patent is extended or adjusted under 35 U.S.C. 154(b) by 0 days.

(21) Appl. No.: 17/050,213

(22) PCT Filed: Apr. 8, 2019

(86) PCT No.: PCT/IL2019/050395
§ 371 (c)(1),
(2) Date: Oct. 23, 2020

(87) PCT Pub. No.: WO2019/207568
PCT Pub. Date: Oct. 31, 2019

(65) Prior Publication Data
US 2021/0243411 A1 Aug. 5, 2021

Related U.S. Application Data

(60) Provisional application No. 62/661,262, filed on Apr. 23, 2018.

(51) Int. Cl.
*H04N 7/18* (2006.01)
*H04N 5/225* (2006.01)
(Continued)

(52) U.S. Cl.
CPC ............ *H04N 7/18* (2013.01); *H04N 5/2256* (2013.01); *H04N 5/238* (2013.01); *H04N 5/23229* (2013.01); *A61B 5/0059* (2013.01)

(58) Field of Classification Search
CPC .... H04N 7/18; H04N 5/2256; H04N 5/23229; H04N 5/238
See application file for complete search history.

(56) References Cited

U.S. PATENT DOCUMENTS 8,638,991 B2   1/2014   Zalevsky et al.
2013/0144137 A1   6/2013   Zalevsky et al.
(Continued)

FOREIGN PATENT DOCUMENTS

WO   2016103271 A2   6/2016
WO   2017/191639 A1   11/2017
WO   2018/150427 A1   8/2018

*Primary Examiner* — Jonathan R Messmore
(74) *Attorney, Agent, or Firm* — Browdy and Neimark, PLLC

(57) ABSTRACT

A system and technique are described, for use in optical monitoring of objects. The system comprising: a collection unit comprising at least one optical arrangement and at least one detector array arranged for defocused collection of light returning from a selected region on the object; and image data collection circuitry configured for receiving electronic signals associated with data piece collected by pixels of the at least one detector array and for generating output data indicative of correlation function between image frames collected by the detector array at two or more different temporal instances. The technique thereby enables determining of correlation between image data pieces with reduced computational complexity.

18 Claims, 20 Drawing Sheets

(51) Int. Cl.
*H04N 5/232* (2006.01)
*H04N 5/238* (2006.01)
*A61B 5/00* (2006.01)

(56) References Cited

U.S. PATENT DOCUMENTS

| | | |
|---|---|---|
| 2014/0148658 A1 | 5/2014 | Zalevsky et al. |
| 2015/0323311 A1 | 11/2015 | Muijs et al. |
| 2018/0376086 A1* | 12/2018 | Tamaki .............. H04N 5/23212 |
| 2019/0155012 A1* | 5/2019 | Stoppe .................. G02B 21/06 |
| 2019/0159701 A1* | 5/2019 | Beiderman .......... A61B 5/7455 |

* cited by examiner

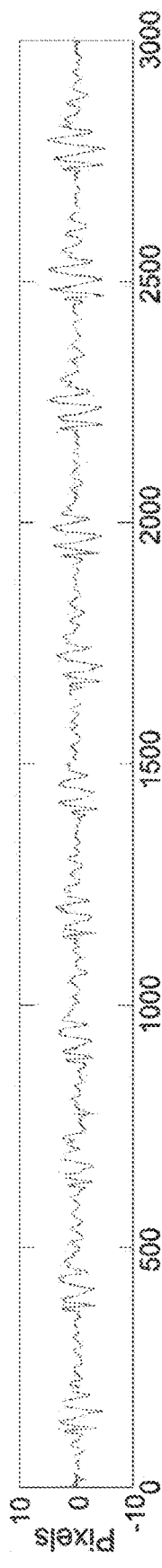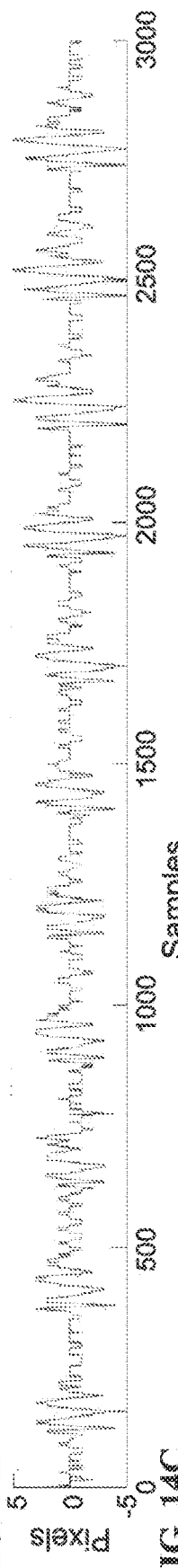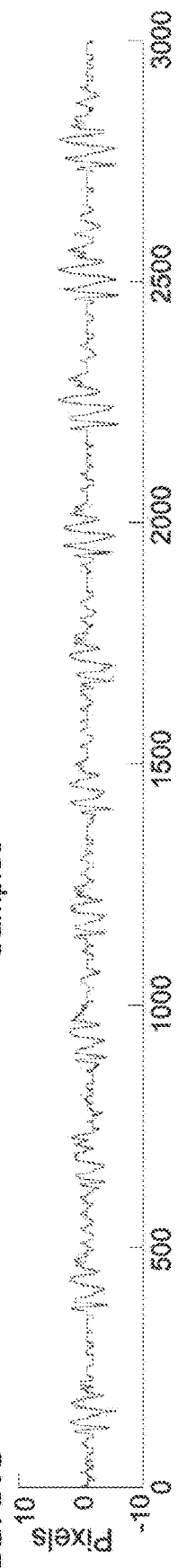

SYSTEM AND METHOD FOR MONITORING A SAMPLE

TECHNOLOGICAL FIELD

The present invention relates to techniques for monitoring a sample or tissue, and is highly relevant for optical monitoring of one or more parameters of a sample or body.

BACKGROUND

Optical monitoring of object or body provide reliable and non-invasive monitoring with limited interference with the target monitored region. Various techniques have been described for optical monitoring enabling collection of one or more parameter of selected sample using temporal variation self-interference pattern of light scattered from the inspected region.

U.S. Pat. No. 8,638,991 presents a method for imaging an object. The method comprises imaging a coherent speckle pattern propagating from an object, using an imaging system being focused on a plane displaced from the object.

US 2013/0144137 and US 2014/0148658 present a system and method for use in monitoring one or more conditions of a subject's body. The system includes a control unit which includes an input port for receiving image data, a memory utility, and a processor utility. The image data is indicative of data measured by a pixel detector array and is in the form of a sequence of speckle patterns generated by a portion of the subject's body in response to illumination thereof by coherent light according to a certain sampling time pattern. The memory utility stores one or more predetermined models, the model comprising data indicative of a relation between one or more measurable parameters and one or more conditions of the subject's body. The processor utility is configured and operable for processing the image data to determine one or more corresponding body conditions; and generating output data indicative of the corresponding body conditions.

General Description

Generally, as indicated above, optical monitoring provides for acquiring parameters of a sample and simple and non-invasive technique. Some efficient optical monitoring techniques utilize correlation in secondary speckle patterns formed in light returning from the inspected region. To this end, one or more inspection regions are illuminated by coherent illumination. Light returning from the region(s) is collected by corresponding collection module generating image data indicative of an intermediate optical plane located between the inspected region and the collection unit, providing image data, which in some configurations relate to defocused image of the inspection region. This image data includes patterns of self-interference of light components scattered from the region, generally known as secondary speckle patterns. The speckle-based monitoring techniques utilizes correlations between speckle patterns collected at a selected sampling rate for determining changes in location, orientation and curvature (generally referred to as tilt) of the inspection regions, indicating nanometric changes and nano-vibrations of the inspected regions.

Accordingly, appropriate monitoring of a sample may be associated with collection of image data pieces, indicative of secondary speckle patterns, at a sufficiently high sampling rate as generally indicated by Nyquist theorem. Thus, determining characteristics of the sample may be associated with processing a plurality of image data pieces and determining suitable correlation functions between consecutive image data pieces, or generally between image data pieces collected at two or more different temporal instances. This may require high processing power and time and limit the system's ability to provide real time analysis of the sample properties.

The present invention provides a system for monitoring parameters of a sample utilizing collection of light components, associated with coherent illumination, that are reflected or scattered from an inspection region for generating one or more sequences of image data pieces indicative of secondary speckle patterns in the collected light. The system utilizes the collected image data for determining correlations between speckle patterns collected at different times (e.g. consecutively collected image data pieces) with reduced processing power and/or time. To this end the system of the present invention utilizes optical, analog and/or partially digital processing of the collected image data for determining correlation functions.

Accordingly, the system of the present invention comprises a collection module comprising optical arrangement and detector array arranged for collection of defocused images of a selected inspection region. The detector array is associated with circuitry configured for providing output electronic data indicative of correlations between image data pieces of two or more different times in accordance with readout operation of the detector array.

In some examples, the detector array may be configured as rolling shutter detector array, and the optical arrangement comprises one or more replication elements configured for directing two or more replications of collected images toward corresponding different regions (pixel rows) of the detector array. The detector array is further associated with circuitry configured to collecting analog output of different pixel rows upon readout and adding analog readout data of pairs of consecutive pixel rows. Further, the circuitry comprises at least two analog-to-digital (A2D) conversion modules having selected different bit thresholds and configured for performing analog-to-digital conversion of the combined analog output of pairs of consecutive pixel rows, providing output data indicative of correlation of pixels of said consecutive pixel rows.

In some other examples, the collection unit may comprise two or more collection sub-units, each comprising optical arrangement and detector array. The collection sub-units are associated with digital signal processing units (DSP) configured for determining integer-pixel correlation functions between image data pieces collected at two or more different times (e.g. consecutive frames). The collection sub-units are configured to provide image data of the inspection region with different defocusing levels providing variation in measurement coefficients enabling to determined weighted average correlation function with high accuracy with given processing powers. The weighted averaging may utilize steering vector data indicative of variations in defocusing levels of the two or more collection sub-units. In some other configurations, the weighted averaging may utilize one or more optimal signal estimation techniques, e g Kalman filtering techniques, for determining optimal data on the tilt of the inspection region.

In yet some other examples, the collection unit may be configured for providing optical correlation of collected image data. To this end the collection unit comprises a spatial light modulating unit, e.g. transmitting SLM or reflecting SLM such as digital mirror device (DMD), enabling modulating light passing through/reflected from, in accordance with selected input. The image data collection circuitry is configured for collecting two frames of defocused image data, provide instructions to the spatial light modulating unit for modulating light in accordance with both frames, and transmit light thereon for collecting image data associated with optical Fourier transform of the frames. The circuitry may be configured to apply a further optical Fourier for determining correlation pick associated with correlation between the two frames.

Thus, according to one broad aspect, the present invention provides a system for use in monitoring an object, the system comprising: a collection unit comprising at least one optical arrangement and at least one detector array arranged for defocused collection of light returning from a selected region on the object; and image data collection circuitry configured for receiving electronic signals associated with data piece collected by pixels of the at least one detector array and for generating output data indicative of correlation function between image frames collected by the detector array at two or more different temporal instances.

The system may comprise, or be associated with, an illumination unit comprising at least one light source unit configured for providing coherent optical illumination onto the selected region on the object.

According to some embodiments of the invention the detector array is operable as a rolling shutter detector; the optical arrangement further comprises an image multiplying unit configured for duplicating collected images onto two or more regions of the detector array; and wherein said image data collection circuitry being associated with analog to digital conversion of output data based on combined data collected in said two or more regions of the detector array, thereby providing digital data associated with image data piece collected at two or more different temporal instances.

The image data collection circuitry may comprise analog data summation line configured for receiving analog collection data from the two or more regions of the detector array and provide summation data of said two or more regions, the analog to digital conversion unit may be operated for converting said summation data using two or more different conversion thresholds thereby providing output data indicative of correlation between said two or more regions of the detector array.

According to some embodiments, the collection unit comprises a spatial light modulation unit configured for applying selected modulation to collected light along optical path between collection optics and the detector array, the image data collection circuitry is configured for receiving data indicative of collected image data pieces and for varying said spatial light modulation unit in accordance with the collected image data to thereby generate correlation between image data piece associated with two or more different temporal instances. The detector array may be located on Fourier plane with respect to the spatial light modulation unit. The spatial light modulation unit may be a digital mirror device (DMD).

The optical arrangement may further comprise a light deflection unit configured for deflecting path of collected light to thereby enabling simultaneous collection of defocused image data indicative of the inspection region and Fourier image data associated with light modulation by the spatial light modulation unit.

The optical arrangement may be configured for directing collected light forming at least two copies of the collected light such that one copy of the collected light is directed at the detector array for collecting image data pieces to thereby enable modulation of the spatial light modulation unit accordingly, and one other copy of collected light is directed at the spatial light modulation unit for interacting with modulation pattern thereof to provide correlation between previously collected image data.

According to yet some embodiments, the collection unit comprises two or more optical arrangements and corresponding two or more detector arrays arranged with different defocusing levels with respect to the selected region on the object, and wherein said image data collection circuitry comprises two or more digital signal processors associated with said two or more detector array and configured for determining variation in collected image data pieces, and an averaging unit configured for receiving input data from said two or more digital signal processors and determining an average variation in collected image data pieces being indicative of correlation function between image data pieces associated with two or more different temporal instances.

The averaging unit of the image data collection circuitry may be configured for determining a weighted average variation associated with correlation function between image data pieces in accordance with pre-stored steering vector corresponding to variations in levels of defocusing between said two or more optical arrangement and the corresponding detector arrays. The averaging unit may also be configured for using fixed weights for determined said weighted average in accordance with said steering vector.

Alternatively, or additionally, the averaging unit may be configured for using adaptive weights for determining said weighted average in accordance with said steering vector. The adaptive weights may be determined in accordance with estimated value of variation in collected image data pieces of the two or more detector arrays.

Generally, the adaptive weights may be determined using signal power covariance estimation associated with variation in collected image data pieces of said two or more detector arrays.

According to yet some embodiments of the invention, the averaging unit of the image data collection circuitry may be configured for determining an optimal estimation of the correlation function by linear or non-linear Kalman filtering technique.

According to one other broad aspect, the present invention provides a method for use in monitoring properties of an object, the method comprising: collecting light returning from a region of the object using defocused optical arrangement and generating at least two defocused image regions onto a detector array; using a rolling shutter readout mode of the detector array and generating at least two temporally shifted image readout pieces associated with said at least two defocused image regions; summing said at least two temporally shifted image readout pieces providing a combined readout data vector; applying analog to digital conversion using two or more different threshold levels and determining difference vector between said two or more conversions, thereby providing data indicative of spatial correlation between said at least two defocused image regions.

According to yet another broad aspect, the present invention provides a system for use in monitoring an object, the system comprising: a collection unit arranged for defocused collection of light returning from a selected region on the object and comprising at least one rolling shutter detector array and an optical arrangement, the optical arrangement comprises an image multiplying unit configured for duplicating collected images onto two or more regions of the detector array; and image data collection circuitry configured comprising analog to digital conversion module, said image data collection circuitry is configured for receiving analog electronic signals associated with data piece collected by pixels of the two or more regions of the detector array and for generating output digital associated with conversion of combined data collected in said two or more regions of the detector array.

The image data collection circuitry may comprise analog data addition line configured for receiving analog collection data from said two or more regions of the detector array and provide summation data of said two or more regions, said analog to digital conversion module being operated for converting said summation data using two or more different conversion thresholds thereby providing output data indicative of correlation between said two or more regions of the detector array.

According to yet another broad aspect, the present invention provides a system for use in monitoring an object, the system comprising an optical arrangement comprising spatial light modulator unit and one or more lens units, a detector array located in Fourier plane with respect to the spatial light modulator unit, light source unit and controlling circuit; the optical arrangement is configured for selectively operating in two collection paths, wherein in a first collection path the optical arrangement is configured for collecting light returning from the object in response to coherent illumination impinging thereon from the light source unit for generating corresponding defocused image on the detector array, and in a second collection path the optical arrangement is configured for directing coherent illumination from the light source unit through the spatial light modulator unit for collecting image data associated with Fourier transformation of pattern provided by the spatial light modulator unit; and wherein said controlling circuit is connected to the detector array and the spatial light modulator unit and configured for receiving image data associated with two collected defocused images and for operating said spatial light modulator unit to thereby apply coded pattern corresponding with combination of said two collected defocused images, thereby enabling detection of optical correlation between said two defocused images.

According to yet another broad aspect, the present invention provides a system for use in monitoring an object, comprising: a collection unit comprising two or more optical arrangements and corresponding two or more detector arrays arranged with different defocusing levels with respect to selected region on the object, and image data collection circuitry comprising two or more digital signal processors associated with said two or more detector arrays configured for determining variation in collected image data pieces and for generating output data indicative of correlation function between image data pieces collected at two or more different times (e.g. frames of different time of collection), and an averaging unit configured for receiving input data from said two or more digital signal processors and determining a weighted average variation indicative of correlation function between image data pieces.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 14A to 14C showing reference, measured and estimated correlation data using linear Kalman filtering respectively;

DETAILED DESCRIPTION OF EMBODIMENTS

Figure 1:
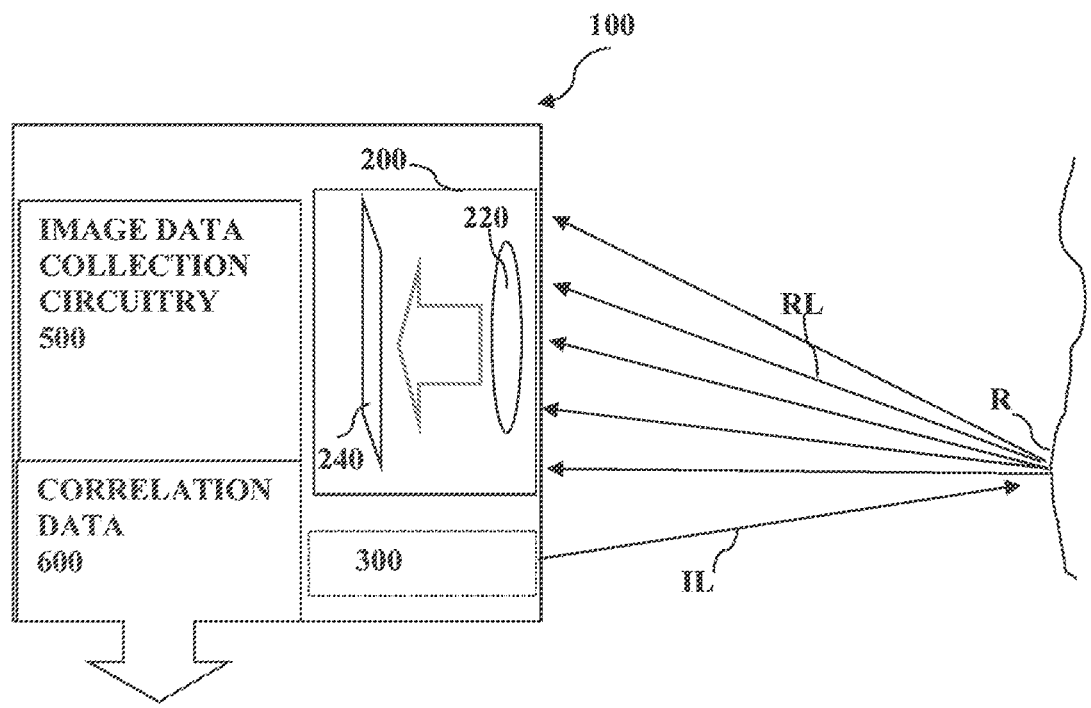
FIG. 1 schematically illustrates a system for monitoring an object according to some embodiments of the invention.

The present invention provides an optical monitoring unit configured for monitoring a selected region of an object using speckle-based monitoring technique. The technique and unit of the present invention are configured for reducing computational complexity associated with determining correlations between speckle patterns in image data pieces of different times (e.g. consecutive frames). FIG. 1 illustrates schematically a system 100 according to some embodiments of the invention. The system 100 includes a collection unit 200 configured for collecting one or more sequences of defocused image data pieces formed by light returning RL from the selected inspection region R; and image data collection circuitry 500 configured for receiving the collected image data pieces and providing output correlation data 600 indicative of spatial correlations between image data pieces of different time of collection. Generally, the system 100 may be associated with or include an illumination unit 300 suitable for providing coherent illumination IL of one or more selected wavelength ranges, and directing the illumination toward the inspection region R.

Generally, as described above, defocused images of light returning from the inspection region in response to coherent illumination impinging thereon, typically include data on speckle patterns formed by self-interference of light components in the returning light RL. Correlations between speckle patterns collected over time provides data on vibrations (including nano-vibrations) of the inspection region, which may be associated with various characteristics and internal processes on or around the inspection region.

Processing of the collected image data pieces for determining correlations between them may be a complex computations task. This is due to the computational process required for determining correlation between two image data pieces as well as due to the desired sampling rate that may range from 10 to 300 frames per second. The system 100 of the present invention and the image data collection circuitry 500 thereof are configured to provide optical and/or electronic arrangement suitable for providing output data indicative of correlations between images utilizing one or more of optical and electronic properties.

Figure 2:
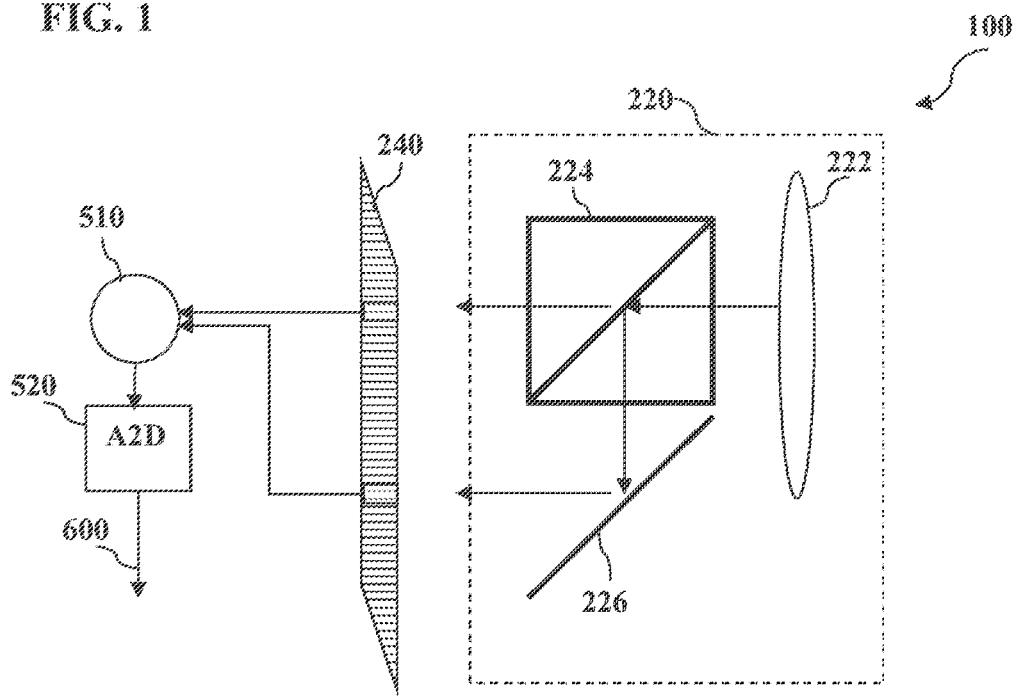
FIG. 2 schematically illustrates a system for monitoring an object using combined analog to digital (A2D) conversion according to some embodiments of the invention.

Reference is made to FIG. 2 providing a partial schematic illustrating of system 100 according to some examples of the invention. In this example, the collection unit includes detector array 240 configured to operate as a rolling shutter detector array, i.e. utilizing raw-by-raw readout scheme, and an optical arrangement 220 including an arrangement for image duplication exemplified herein by light splitter 224 and reflector 226. The image data collection circuitry 500 includes at least one signal combiner 510 and at least one analog-to-digital (A2D) conversion unit 520. These configurations utilize shifted image collection regions and duplication of the collected light (image) to provide correlation between image data portions associated with image data pieces collected at different times (e.g. consecutive frames). More specifically, the image duplication arrangement provides two or more duplications of collected light onto corresponding two or more regions of the detector array 240, this is while the rolling shutter configuration of the detector array 240 results in that image data of the two or more regions of the detector array 240 are indicative of light collected at different time slots providing different frames. The image data collection circuitry is configured for utilizing operation of the A2D conversion unit 520 for providing digital data indicative of correlation between such different frames.

Figure 3:
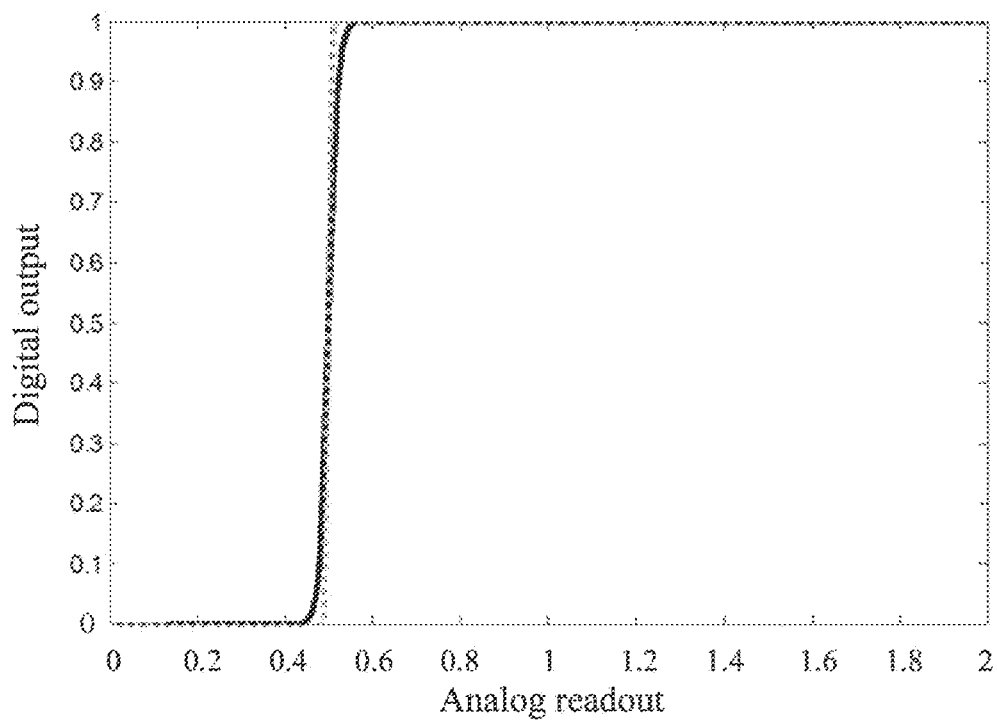
FIG. 3 shows an example of A2D conversion curve and approximation according to some embodiments of the present invention.

In this connection, analog to digital conversion may be considered as nonlinear operator D providing digital conversion of an analog value A received from the sensor. Given that the transistors and the logic gates that perform the A2D conversion have a continuous output function and not fully digital, the A2D operation for one bit can be presented as:

$$D = 1 - \frac{1}{1+\exp((A-th)\beta)} = \frac{1}{1+\exp(-(A-th)\beta)} \quad \text{(equation 1)}$$

Where th is a selected conversion threshold value and $\beta$ is a digitizing conversion parameter. For simplicity, the following analysis considers normalized values, i.e. the range of values for A is between 0 and 1 and th=0.5. The value of $\beta$ is assigned to be about 100 to get good physical modeling of the A2D conversion. FIG. 3 shows a graph (solid line) of the output digital value D for various values of analog input A using selected threshold parameter th=0.5 and digitizing parameter $\beta$=100 and dotted plot showing desired optimal conversion graph.

Expansion of the digitizing function of equation 1 around the value of A=th provides:

$$D_+ = 1 - \frac{1}{1+\exp((A-th)\beta)} = \frac{1}{1+\exp(-(A-th)\beta)} \quad \text{(equation 2)}$$

$$\approx 1 - \exp(-(A-th)\beta) = (A-th)\beta - \frac{(A-th)^2\beta^2}{2} + \ldots$$

For A>th and $$D_- = 1 - \frac{1}{1+\exp((A-th)\beta)} \approx 1 - (1-\exp((A-th)\beta)) = \quad \text{(equation 3)}$$

$$\exp((A-th)\beta)$$

$$= 1 + (A-th)\beta + \frac{(A-th)^2\beta^2}{2} + \ldots$$

For A<th. Using two A2D conversions with slightly different thresholds th and subtracting the two obtained results can be approximated as:

$$D_- - D_+ \approx 1 + (A-th)^2\beta^2 \quad \text{(equation 4)}$$

This operation of A2D conversion is done for every spatial pixel of the camera. However, the use of rolling shutter operability of the detector array provides the analog output as:

$$A(x) = g^{(r1)}(x) + g^{(r2)}(x - \Delta x) \quad \text{(equation 5)}$$

where $g^{(r1)}(x)$ is the spatial information of the collected image data (portion of speckle pattern) at time $t_1$ and $g^{(r2)}(x-\Delta x)$ is the spatial information of the collected image data at time $t_2$ shifted in space by amount of $\Delta x$. Thus, the overall digital output we obtain equals to:

$$D_- - D_+ = (1 + th^2\beta^2) + 2\beta^2 g^{(r1)}(x)g^{(r2)}(x-\Delta x) + \beta^2(g^{(r1)}(x))^2 + \beta^2(g^{(r2)}(x+\Delta x))^2 - 2th\beta^2(g^{(r1)}(x) + g^{(r2)}(x-\Delta x)) \quad \text{(equation 6)}$$

Summing the pixels related to the spatial information (performing summation over the columns of the rolling shutter detector array) provides:

$$\int (D_- - D_+) dx = \ldots 2\beta^2 \int g^{(r1)}(x) g^{(r2)}(x-\Delta x) dx + \ldots \quad \text{(equation 7)}$$

The output provided by equation 7 is composed from a constant, terms equivalent to the energy of every speckle image and a correlation expression for shift value $\Delta x$.

Accordingly, the image data processing circuit may be configured for summing analog output of rows associated with the two or more different regions of the detector array 240 and transmit the resulting analog data to suitable pair of A2D conversion, operated by a single A2D conversion unit 520 or two or more such conversion units. The resulting output may be further summed along the columns providing output data 600 indicative of correlation between image data pieces collected with certain time difference between them.

Figure 4:
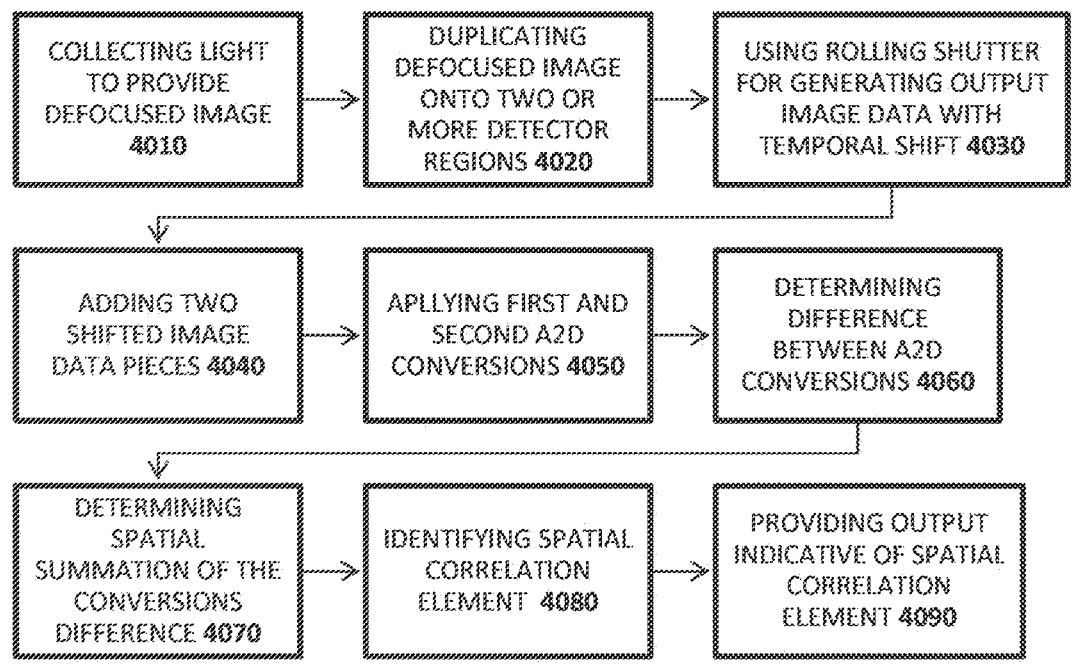
FIG. 4 shows a flow diagram exemplifying a technique for determining correlations between image data pieces according to some embodiments of the present invention.

The general scheme exemplifying the technique for monitoring an object using the system of FIG. 2 is exemplified in FIG. 4. As shown, the technique includes collecting light returning from an object 4010 in response to coherent illumination of a region of the object. The light is collected to provide defocused image on a detector array to thereby generate image data pieces associated with secondary speckle patterns, rather than real space image of the inspected region. Along optical path of the collected light, the technique utilizes duplicating/splitting the collected light for forming two or more defocused images onto corresponding two or more regions of the detector array 4020, such two or more regions generally relate to different rows of the detector array. The use of rolling shutter detector array 4030 provide output image data with temporal shift between image data pieces collected from the two or more regions, from the corresponding rows Manipulating the collected readout of the detector array for adding data about two shifted images 4040, with selected spatial shifts, and applying first and second analog to digital conversions 4050 with two different conversion thresholds. As described above, in equations 6 and 7, determining difference between the analog to digital conversions 4060 and spatial summation for different spatial shifts 4070 provides output conversion data indicative of correlation element 4080. Generally, the determined correlation elements are used for providing output data for further processing 4090 enabling to determine various properties of the object.

Figure 5:
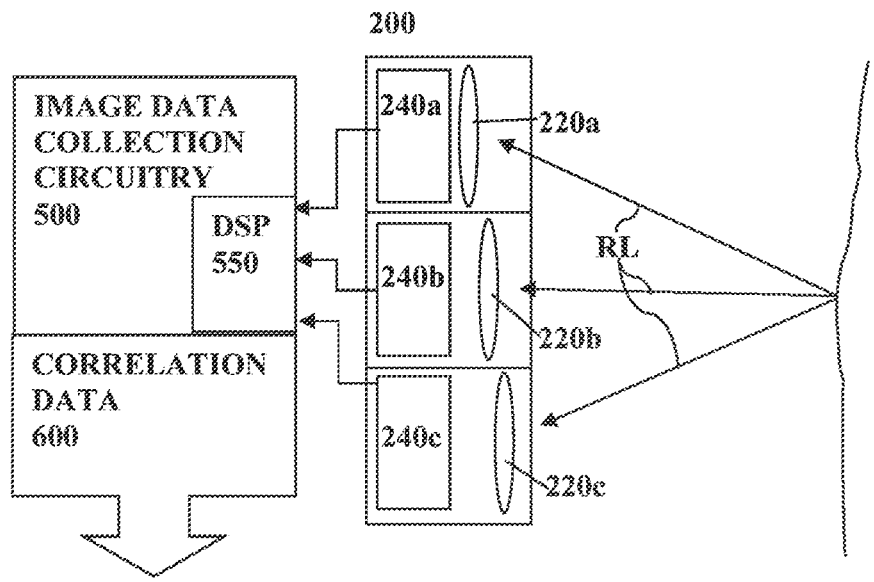
FIG. 5 illustrates schematically a system for monitoring an object and determining correlation function between image data pieces using two or more collection sub units according to some embodiments of the present invention.

An additional example of the present invention utilizes two or more light collection arrangements generally including associated digital processing (e.g. such as signal processing used in optical mouse for motion tracking). Reference is made to FIG. 5 exemplifying system wherein collection unit 200 includes two or more (in this example three) collection arrangements formed by lens arrangements 220a, 220b and 220c and corresponding detector arrays 240a, 240b and 240c. the image data processing circuit 500 includes one or more digital signal processors (DSP) 550 configured for determining shift between image data pieces collected at different times, similarly to typically DSP used in optical mouse for controlling location/movement of cursor in personal computing systems.

Generally, the DSP units 550 are configured to provide output indicative of position corresponding to the x-y coordinates in integer values. More specifically, general correlation between digitized image data pieces provides pixelated correlation data (i.e. in integer step values based on discrete nature of the input data). Various techniques are often used for extrapolating sub-pixel data from the so-determined correlation data. However, such techniques typically require additional processing power, time and increased energy consumption. Further, the sensitivity achieved by integer value correlation data is generally sufficient for use as input and controlling cursor's movement. This sensitivity may be insufficient of detector nanovibrations at the inspection region and introduce rounding errors into the correlation function. The technique of the present invention overcomes this issue, using two or more collection arrangement having different defocus levels. As shown in FIG. 5, collection unit 200 includes three collection sub-units exemplified by optical arrangements 220a, 220b and 220c corresponding detector arrays 240a, 240b and 240c. the collection sub-units are formed with different defocusing levels, exemplified in the figure by different distances between the optical arrangements 220a, 220b and 220c and the associated detector arrays 240a, 240b and 240c.

Figure 6:
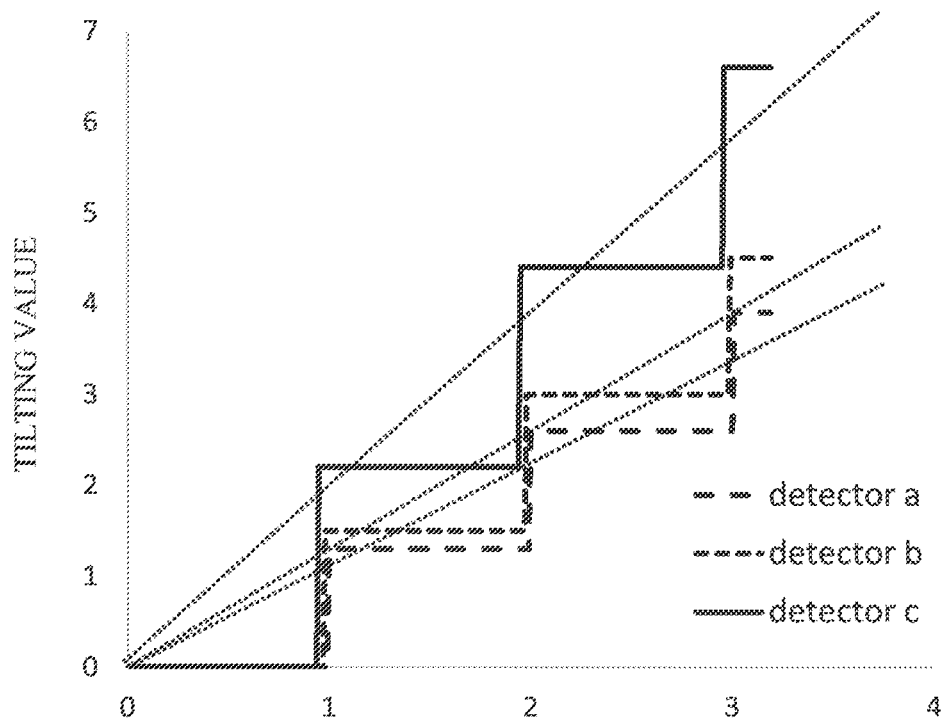
FIG. 6 exemplifies some concepts of steering vector and weighted averaging according to some embodiment of the present invention.

The output of the DSP 550 relates to a linear relation between tilting level and spatial (in x-y plane) shifts determined by correlating different image data piece along discrete pixels of the images (i.e. in integer steps). The level of defocusing of each collection sub-unit sets a corresponding proportional ratio to this relation. The use of two or more differently defocused images and corresponding DSP processing provides two or more different linear translations between x-y position of the correlation function and the tilting of the object enabling sub-pixel estimation of the tilt (based on correlation) and reduce rounding errors. By averaging the output shift data from the different collection sub-units, typically with suitable weights and scales, the present technique provides sub pixel super resolving tilting extraction even if the typical shift outputs are of integer values. FIG. 6 illustrates exemplary output shift data of three detector arrays 240a, 240b and 240c (marked as detectors a, b, and c) having different defocusing levels. The image data processing circuit 500 is further configured for determining a weighted average shift data with sub-pixel resolution to determine sufficiently sensitive output correlation data 600.

Generally, the DSP 550 output data associated with each one of detector arrays 240a, 240b and 240c, is normalized in accordance with defocusing level providing both variations in the sensitivity to shifts in collected image data and to the output tilting values. Accordingly, interpolation/averaging between the two or more corresponding output values provides a non-integer estimation of the actual tilt at the inspection region. The interpolation or averaging is provided for determining actual data on variation in orientation/location of the inspection region, herein referred to as tilt, with minimization of rounding errors associated with digitizing the correlation function based on pixels of the detector arrays.

Figure 7A:
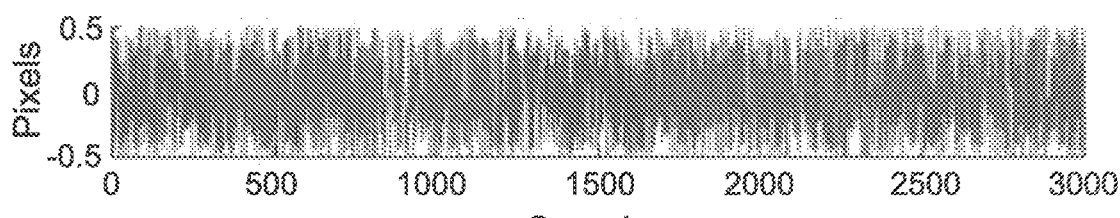
FIGS. 7A to 7F show rounding errors associated with integer-value correlations with respect to reference sub-pixel correlation using small, medium and large defocusing values.
Figure 7B:
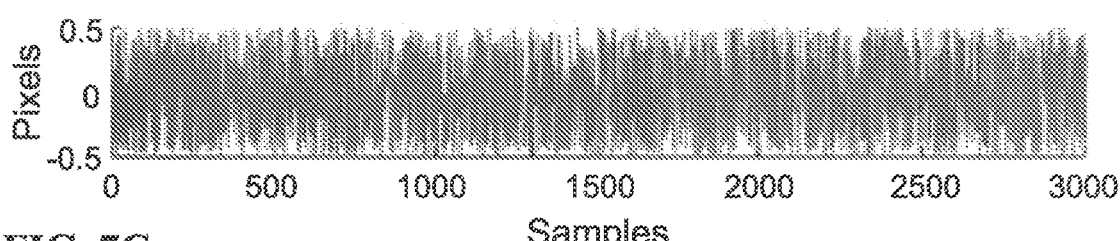
Figure 7C:
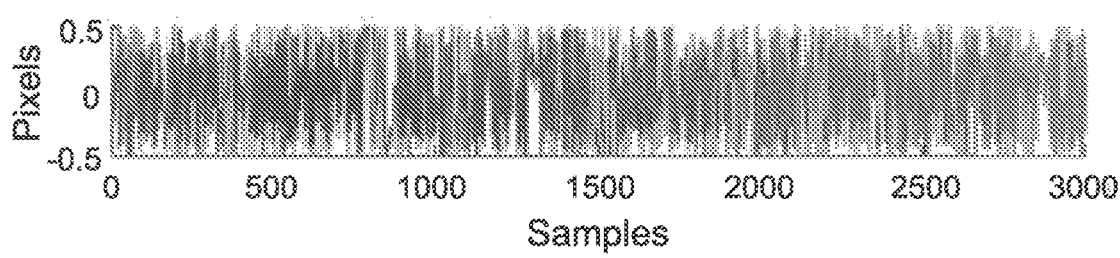
Figure 7D:
Figure 7E:
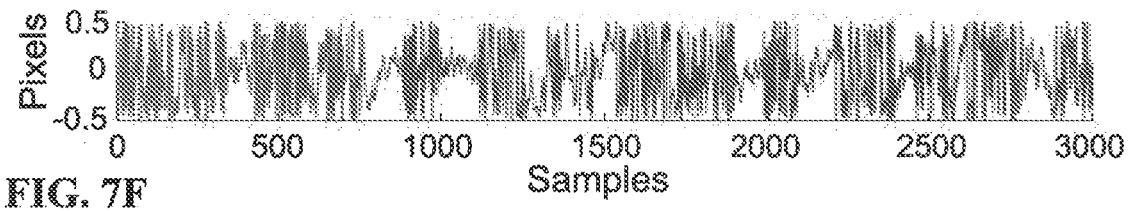
Figure 7F:
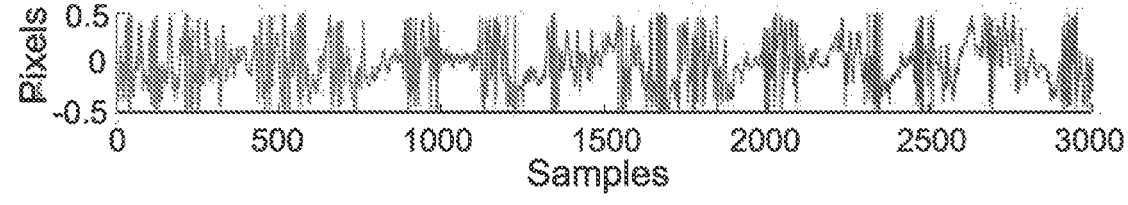

To this end, given actual tilt defined in time increments i as $s_i$, and the correlation determined by the DSP 550 for image data collected by one of the detector arrays is described as $y_i$, the relation can be described as $y_i = a \cdot s_i + v_i$, where $v_i$ describes random error resulting from the pixelated nature of the detector array and accordingly of the determined correlation between image data pieces, a is a steering vector associated with defocusing of the collection units (i.e. relation between the optical arrangement and detector array) determined as:

$$a=[1,d_2/d_1,d_3/d_1,\ldots,d_N/d_1,]$$ (equation 8)

where $d_j$ is defocusing level of collection sub-unit j. The rounding error $v_i$ may typically be uncorrelated between different detector arrays, and randomly distributed. Additionally, the rounding errors may be considered independent of the desired tilt signal data. It should be noted that in cases where the tilt signal $s_i$ is relatively small, i.e. corresponding with correlation shift value of 0.5 pixel of the detector array or less, the distribution of the rounding error $v_i$ is concentrated close to zero. Reference is made to FIGS. 7A to 7F showing rounding error values for tilt along x axis (FIGS. 7A-7C) and y axis (FIG. 7D-7F) for collection using different defocusing levels. FIGS. 7A and 7D show rounding error values for large defocusing, FIGS. 7B and 7E shows rounding error values for medium defocusing and FIGS. 7C and 7F shows rounding error values for small defocusing. The rounding error is determined with respect to reference subpixel interpolation of the correlation function.

Accordingly, a suitable averaging of correlation data $y_i^j$, determined in accordance with image data pieces collected by the different detectors j, may be determined by weighted average using a weighting vector W providing:

$$S_i = W^T y_i^j$$ (equation 9)

where $S_i$ is the estimate tilt signal with minimized rounding errors. The inventors of the present invention have identified the following approaches as suitable for use in determining weighting vector W.

Fixed weights by weighted averaging: the weighting vector W is determined in accordance with steering vector a such that $w=a/\Sigma_j a$.

Fixed weights conventional beamforming: the weighting vector W is determined in accordance with normalized steering vector a to maximize power output, providing $w=a/\|a\|$.

Adaptive weighting for minimum noise power (Capon beamforming): this technique utilizes the measured data $y_i^j$ for determining the weighting values of W. This technique is based on optimization of $$\min_w E\{w^T y y^T w\},$$

given that $w^T a = 1$, and provides $$w = \frac{R^{-1} a}{a^T R^{-1} a},$$

where $R = E\{y y^T\}$. In this context, $E\{x\}$ refers to expected value associated with probability distribution of the parameter x. The covariance matrix R may be replaced by an approximated sampled covariance matrix formed by the vectors $y_i^j$ such that $Y=[y_1, y_2, \ldots y_N]$ providing $$R \cong \frac{1}{M} Y Y^T.$$

Adaptive weighting for maximal signal to noise ratio (SNR): This technique utilized statistic parameters of the noise to maximize the SNR. Generally, this provides $$w = \frac{R_v^{-1} a}{a^T R_v^{-1} a},$$

where $R_v = E\{v v^T\}$. The noise v, corresponding with rounding errors, generally follows known statistical behavior. More specifically, it is assumed that the rounding errors are random errors having uniform distribution in the range [0,1]. This provides the suitable estimation of $R_v = \sigma_q^2 I$, where $$\sigma_q^2 = \frac{0.5^2}{12}.$$

It should be toned that such estimation provides this weighting technique as fixed weights. Alternative estimation for W utilizes adaptive scheme using signal power covariance estimation (eigenvector beamforming) providing $R = P_s a a^T + \sigma^2 I$, where $P_s$ is the average signal power (energy) and $\sigma^2$ is estimated by eigenvector decomposition of R as mean value of the N−1 smaller eignevalues, where the larger eigenvalue is given by $P_s$.

Figure 8A:
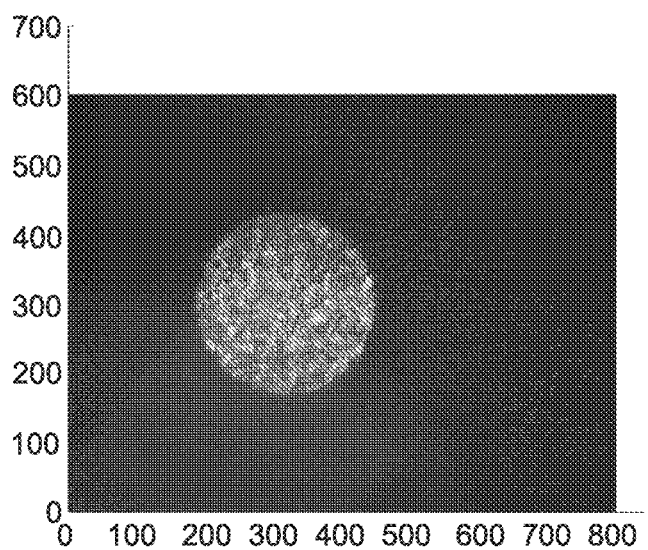
FIGS. 8A to 8C show collected defocused image data associated with an illumination spot with large, medium and small defocusing levels respectively.
Figure 8B:
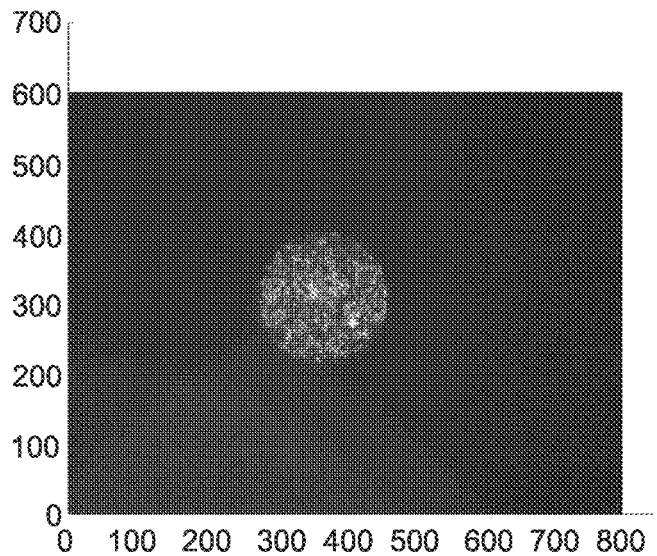
Figure 8C:
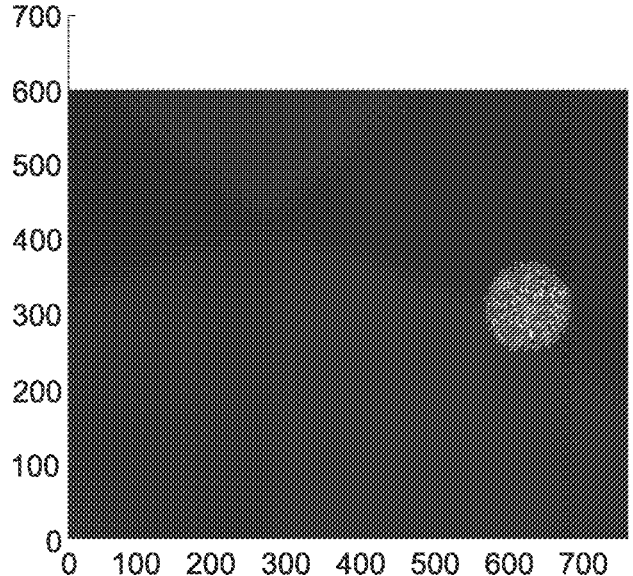
Figure 9A:
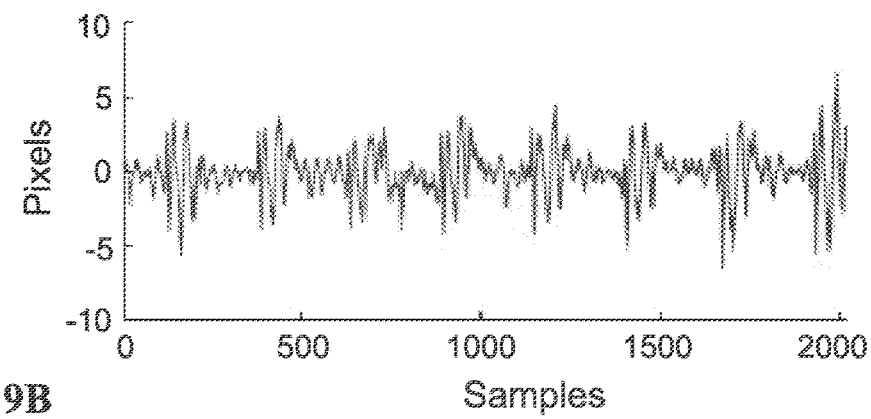
FIGS. 9A to 9D show reconstructed correlation data using fixed weighting technique by weighted averaging along x and y axes (FIGS. 9A and 9B respectively) and corresponding errors histogram with respect to the reference sub-pixel correlation data (FIGS. 9C and 9D respectively)
Figure 9B:
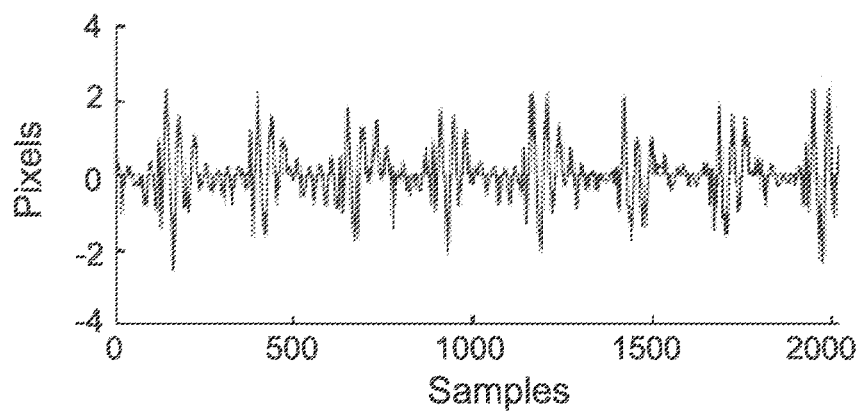
Figure 9C:
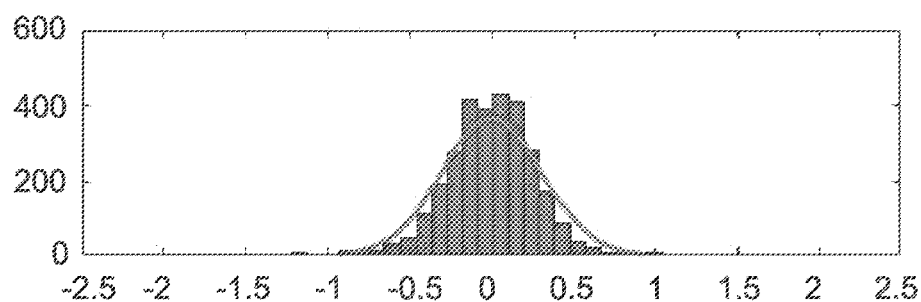
Figure 9D:
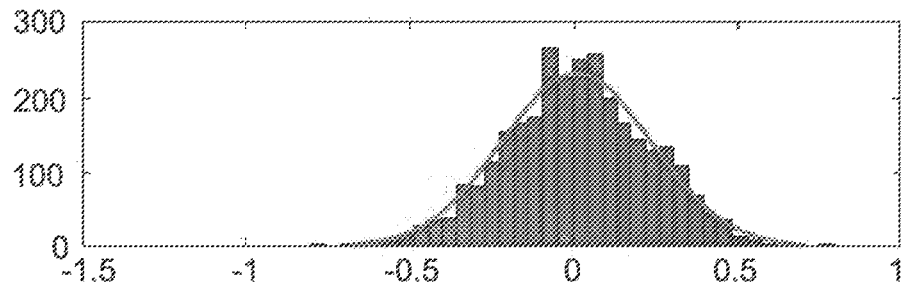
Figure 10A:
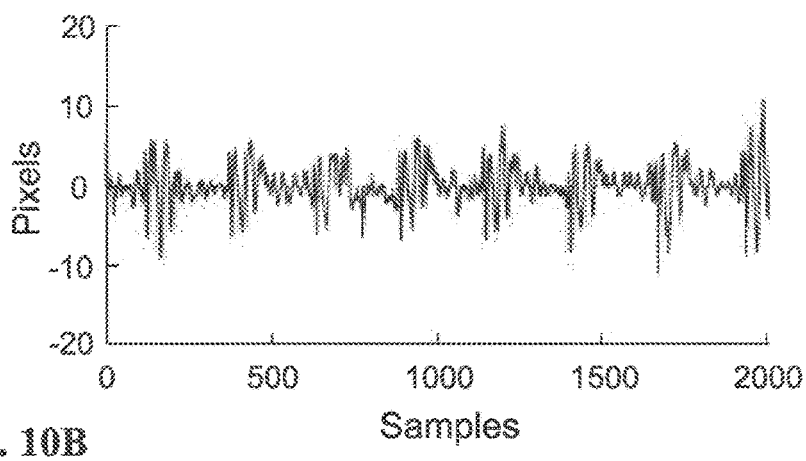
FIGS. 10A to 10D show reconstructed correlation data using fixed weighting technique using conventional beamforming technique along x and y axes (FIGS. 10A and 10B respectively) and corresponding errors histogram with respect to the reference sub-pixel correlation data (FIGS. 10C and 10D respectively)
Figure 10B:
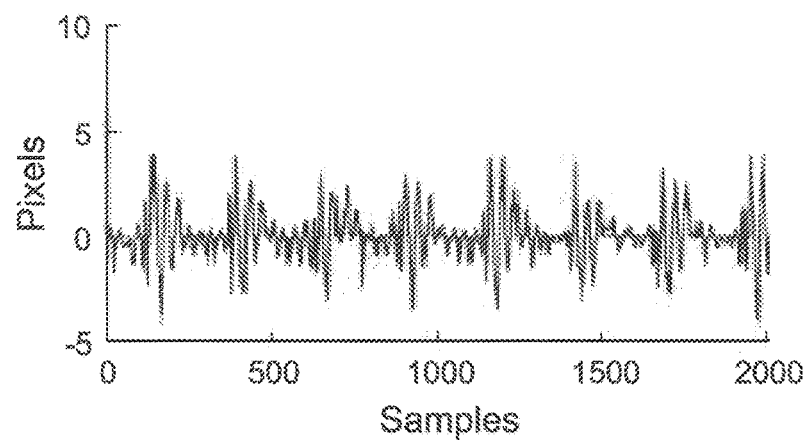
Figure 10C:
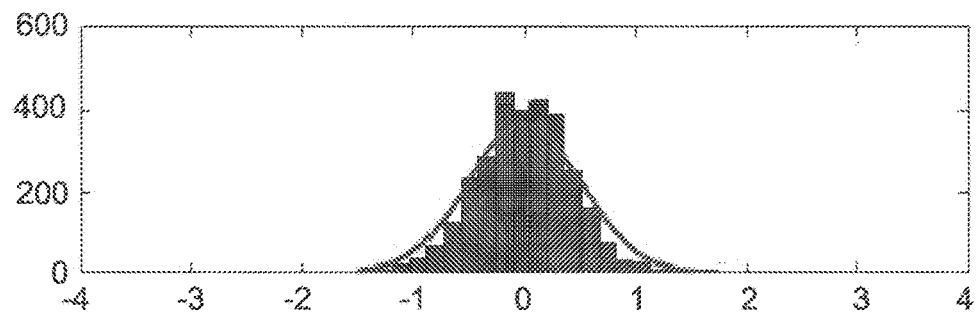
Figure 10D:
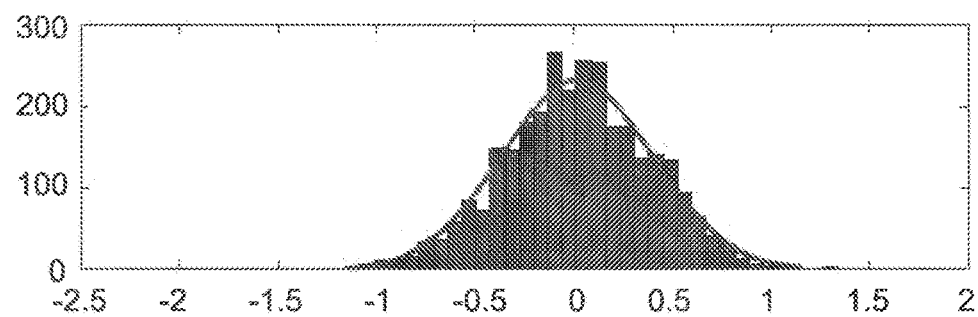
Figure 11A:
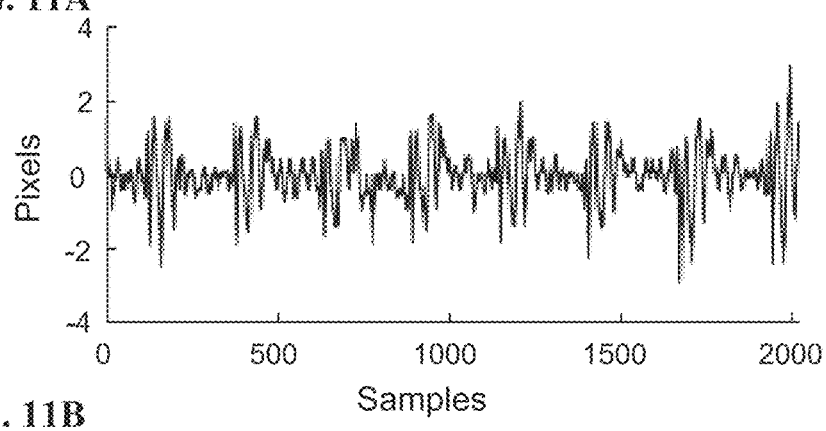
FIGS. 11A to 11D show reconstructed correlation data using adaptive weighting technique using Capon beamforming technique along x and y axes (FIGS. 11A and 11B respectively) and corresponding errors histogram with respect to the reference sub-pixel correlation data (FIGS. 11C and 11D respectively)
Figure 11B:
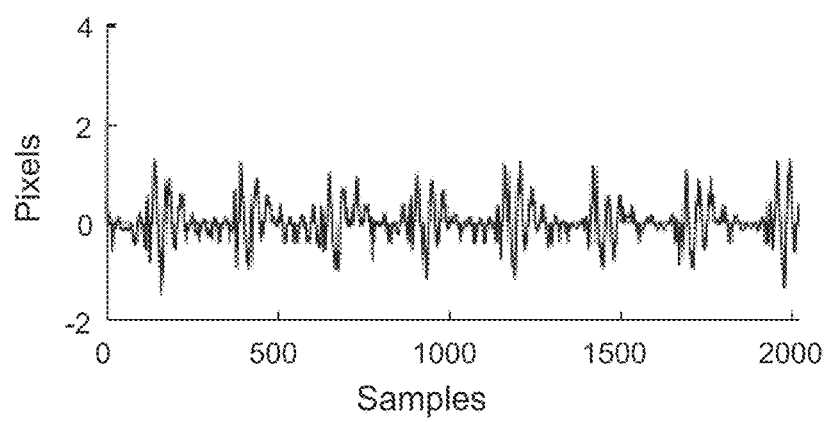
Figure 11C:
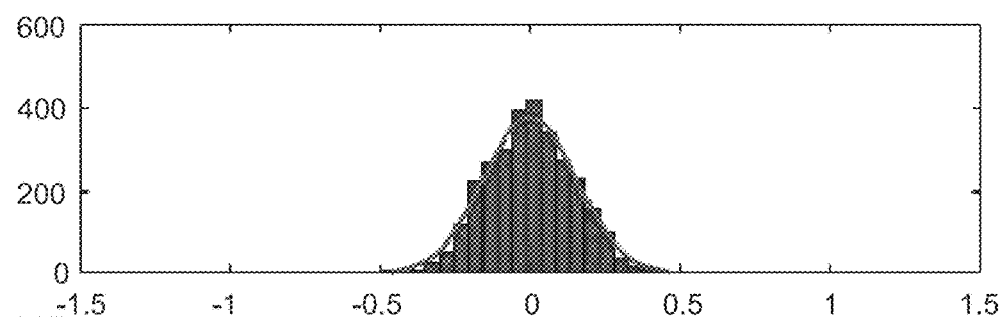
Figure 11D:
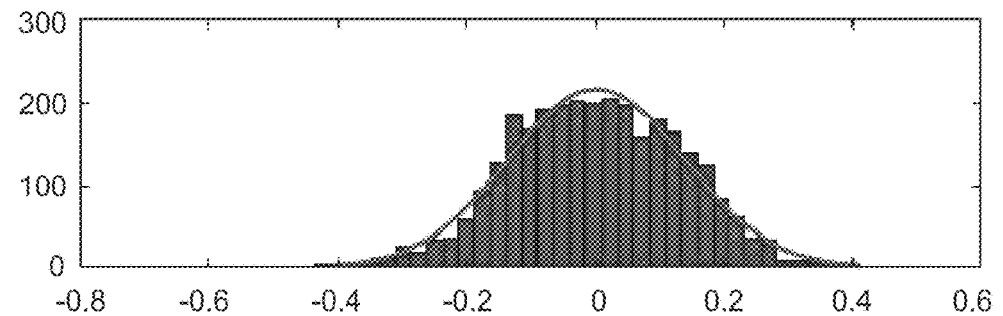
Figure 12A:
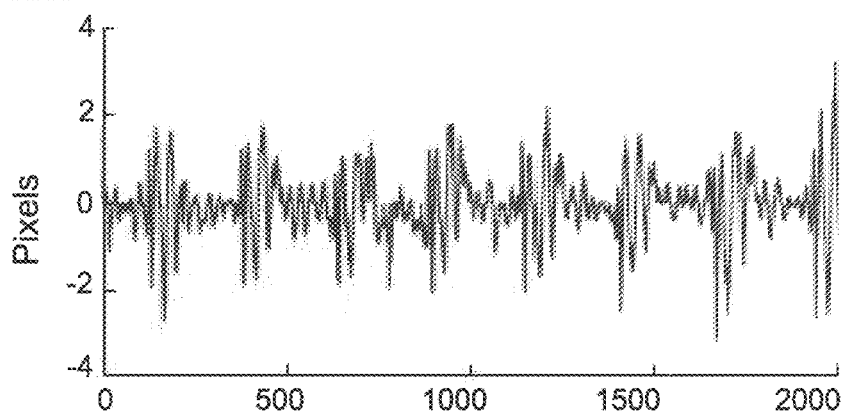
FIGS. 12A to 12D show reconstructed correlation data using adaptive weighting technique using maximum SNR beamforming technique along x and y axes (FIGS. 12A and 12B respectively) and corresponding errors histogram with respect to the reference sub-pixel correlation data (FIGS. 12C and 12D respectively)
Figure 12B:
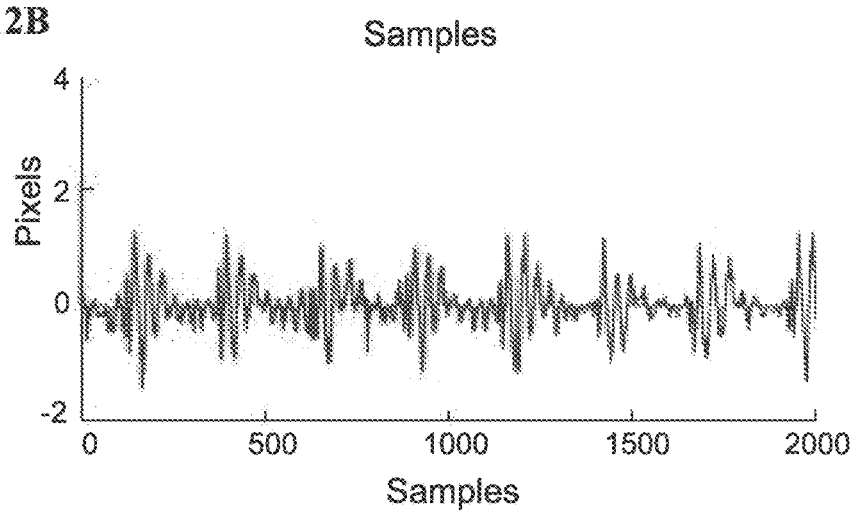
Figure 12C:
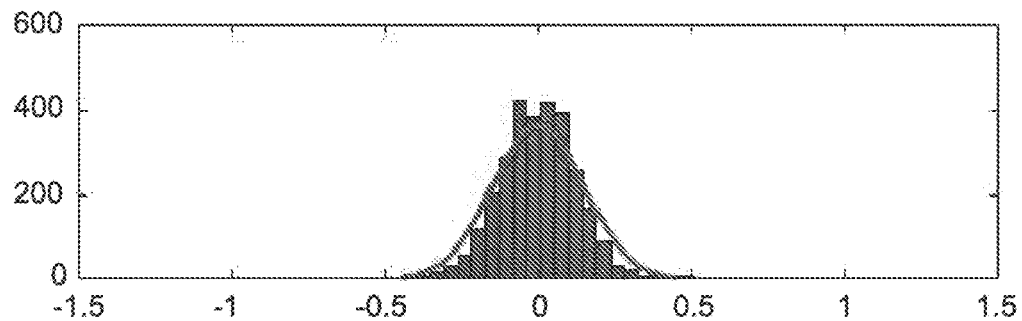
Figure 12D:
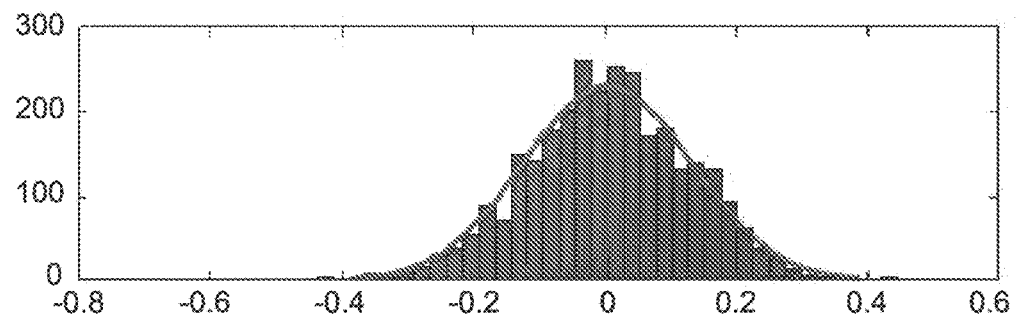

Reference is made to FIGS. 8A to 8C exemplifying defocused image data pieces collected at three defocusing levels from a common inspection region. The relative defocusing levels and collection units' angles were selected arbitrarily. It should be noted that the steering vector a is typically pre-known as relating to actual design of the system. However, the values of the steering vector may be determined using collected image data in accordance with ratios of diameters of the spot sizes between each collection sub-unit. Moreover, the steering vector may include different defocusing ratios along x and y axes as the angular location of the collection sub-units may differ. In this example, the defocusing ratios have been determined based on spot diameters as $a^x=[1,2.04,2.52]$ and $a^y=[1,1.66,2.25]$.

Correlation data is determined based on sequences of images collected by the three collection sub units as exemplified in FIGS. 8A-8C. To this end, for each sequence a small window of 64×64 pixels was extracted around estimated center of mass of the spot of collected light. The shifts and variation of the speckle patterns were estimated using correlation between the 64×64 pixels windows in adjacent time frames (implemented in 2D-to-1D correlation-based procedure) for sequence of each collection sub unit. Sub-pixel correlation estimation based on the sub-unit having lowest defocusing, exemplified in FIG. 8A, is selected as reference signal. For every sensor, integer pixel correlation is determined to provide movement estimation to determine weighted average movement estimation as described above using different weighted beamforming techniques.

Figure 13A:
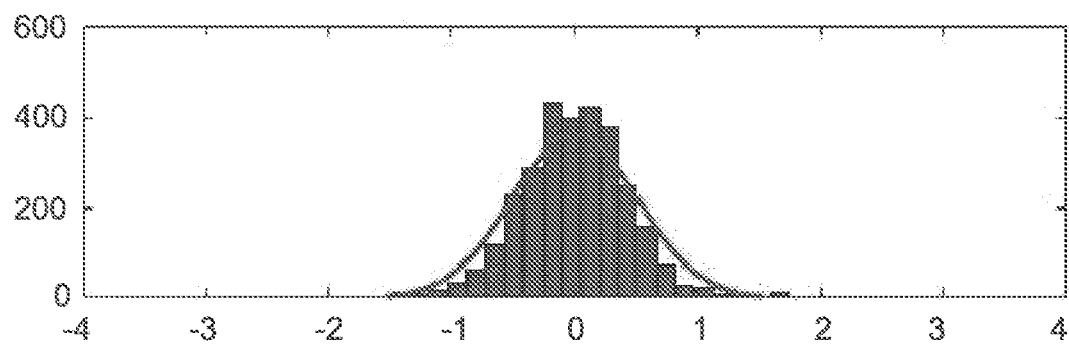
FIGS. 13A and 13B show error histogram for eigenvector beamforming, which is a fixed weights variation of the maximal SNR technique.
Figure 13B:
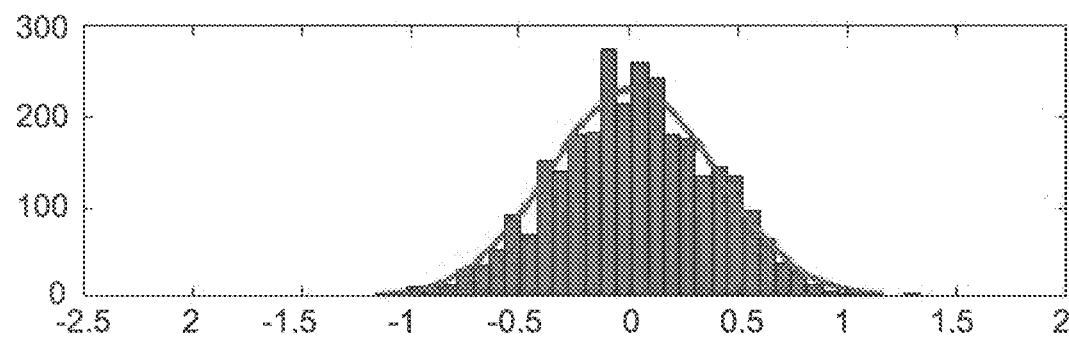

Reference is made to FIGS. 9A-9D, 10A-10D, 11A-11D, 12A-12D and 13A-13B showing correlation data using different weighting by configurations and corresponding errors histogram with respect to the reference sub-pixel correlation data. FIGS. 9A-9D show reconstructed signal results provided by fixed weighting by weighted averaging, FIGS. 10A-10D show reconstructed signal results using conventional beamforming fixed weights as described above, FIGS. 11A-11D show reconstructed signal results using adaptive weighting for minimum noise power and FIGS. 12A-12D show reconstructed signal results using adaptive weighting for maximal SNR. FIGS. 13A and 13B show error histogram relating to reconstructed signal using for eigenvector beamforming along X and Y axes respectively. As indicated above, eigenvector beamforming is a fixed weights variation of the maximal SNR technique.

FIGS. 9A and 9B and FIGS. 10A and 10B show estimated correlation shifts along the x and y axes for fixed weighting by weighted averaging and using conventional beamforming respectively; FIGS. 9C and 9D and FIGS. 10C and 10D show respective error histograms with respect to sub-pixel correlation reference data. As shown, the correlation functions show general agreement between the two weighting techniques and the error histograms show normal distribution with standard deviation of 0.31 and 0.23 for the weighted averaging and 0.51 and 0.38 for the conventional beamforming along the x and y axes. Although the structure of the weighting vector W is almost similar, the weighted averaging provided slightly better results (in the sense of error variance) than conventional beamforming. This is due to different distribution of weights between the collection sub-units.

FIGS. 11A and 11B and FIGS. 12A and 12B show similar estimated correlation shifts based on Capon beamforming and maximum SNR beamforming respectively; FIGS. 11C and 11D and FIGS. 12C and 12D, as well as FIGS. 13A and 13B show respective error histograms with respect to the sub-pixel correlation reference data. It should be noted that the graphs shown in FIGS. 12A to 12D relate to the eigenvector decomposition of $R=P_s aa^T+\sigma^2 I$ providing generally an adaptive weighting technique. The error histograms of FIGS. 13A and 13B relate to the fixed variation of the technique using $R_v=\sigma_q^2 I$ and thus is substantially similar to the conventional beamforming results.

Generally, these experimental results illustrate that even though the scaling factor of the adaptive weighting technique may vary, many practical cases it is relatively close to unity and may at times vary within the range of 0.5-2; the adaptive weighting estimation techniques provided standard deviation values of the errors to be 0.16, 0.14, 0.15, and 0.13, thus providing greater accuracy and increased SNR with respect to the fixed weight techniques. It should also be noted that these results have been reproduced in additional experiments providing the same characteristics.

According to additional examples of the present technique, the integer-value correlation data may be used to provide high accuracy output correlation data using one or more optimal value estimation techniques. For example, integer-value correlation data associated with image data collected by the two or more collection sub-units may be combined using suitable optimal value estimation techniques, such as Kalman Filter, for determining output correlation data indicative of tilt of the inspection region.

To this end, referring back to FIG. 5, the image data collection circuitry 500 utilizes integer value correlation data determined by the DPS 550 for each of the two or more collection sub-units, e.g. received from detector arrays 240A, 240B and 240C. The image data collection circuitry 500 utilizes a suitable model pre-stored in a corresponding storage utility and determines optimal estimated data on correlation function between image data pieces collected at different times using selected optimal value estimation techniques such as linear or nonlinear Kalman filtering technique.

In some configurations, the pre-stored model may be based on almost constant velocity (ACV) model including one or more noise terms associated with at least one of measurement noise and rounding noise (resulting from pixelated nature of the correlations functions determined by the DSP 550). The noise terms may generally be modeled as zero mean Gaussian noise having selected variance $\sigma_w^2$. More specifically, the ACV model may be as follows:

$$\begin{bmatrix} x \\ v \end{bmatrix}_k = \begin{bmatrix} 1 & \Delta t \\ 0 & 1 \end{bmatrix} \begin{bmatrix} x \\ v \end{bmatrix}_{k-1} + w_k, \quad \text{(equation 10)}$$

$$w_k \sim N(0, Q), = \begin{bmatrix} \frac{\Delta t^4}{4} & \frac{\Delta t^3}{2} \\ \frac{\Delta t^3}{2} & \Delta t^2 \end{bmatrix} \sigma_w^2$$

where $x_k$ is the tilt value (desired correlation shift), $v_k$ is the modeled velocity, zit is time increment between image data pieces and $w_k$ is modeled measurement noise. The measurement channel model may be linear or non-linear, and may generally include a rounding noise term indicating the pixelated nature of the correlation data. A linear representation of the measurement data indicates that $$y_k = \begin{bmatrix} 1 & 0 \end{bmatrix} \begin{bmatrix} x \\ v \end{bmatrix}_k + n_k, \quad \text{(equation 11)}$$

Where $y_k$ is the determined correlation shift between different image data pieces and $n_k$ is the corresponding rounding noise, which may typically have uniform probability distribution in the range [−0.5,0.5] as indicated above. Additionally, the measurement model may have non-linear quantization form including a quantization mapping M, providing:

$$\widetilde{y_k} = M(y_k) \quad \text{(equation 12)}$$

Generally, the estimation technique, utilizes input data in the form of measurement results $y_k$ from the DSP 550 in accordance with image data pieces collected by the two or more collection sub-units, and utilizes the input measurement data for estimating optimal correlation shift data $x_k$. The processing technique of Kalman filtering is generally known and this will not be described herein in details, other than to note that the process is based on main two operational steps including prediction or time-update, in which estimated values of the desired signal $x_{k+1}$ are predicted based on the selected model and data on $x_k$; and an update, or measurement update, in which the predicted value and corresponding factors are updated in view of the measured data $y_{k+1}$. It should be noted that the estimation technique using two or more measurement inputs (correlation data $y_k$) is based on introduction of the two or more measurement data elements in the measurement update stage. In this case the two or more measurement data elements are considered to follow similar model, while allowing variation in the noise elements and the velocity.

Figure 15A:
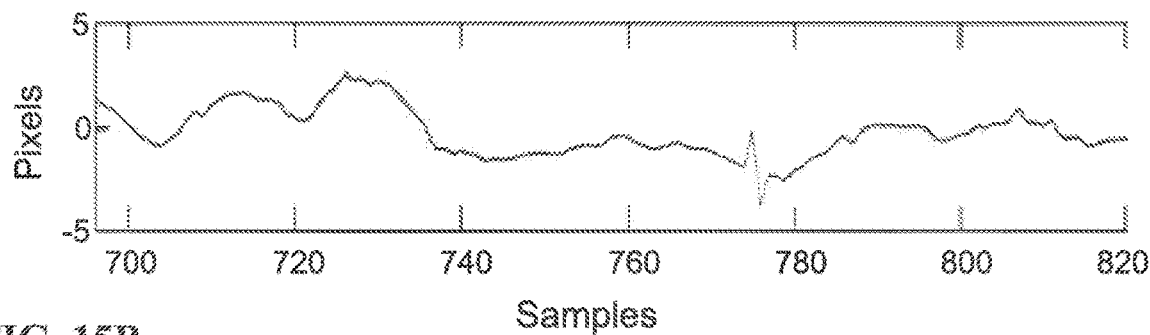
FIGS. 15A to 15D show enlarge plots of the reference, measured and estimated correlation data using linear Kalman filtering shown in FIGS. 14A to 14C and resemblance between the reference and estimated correlation sifts respectively.
Figure 15B:
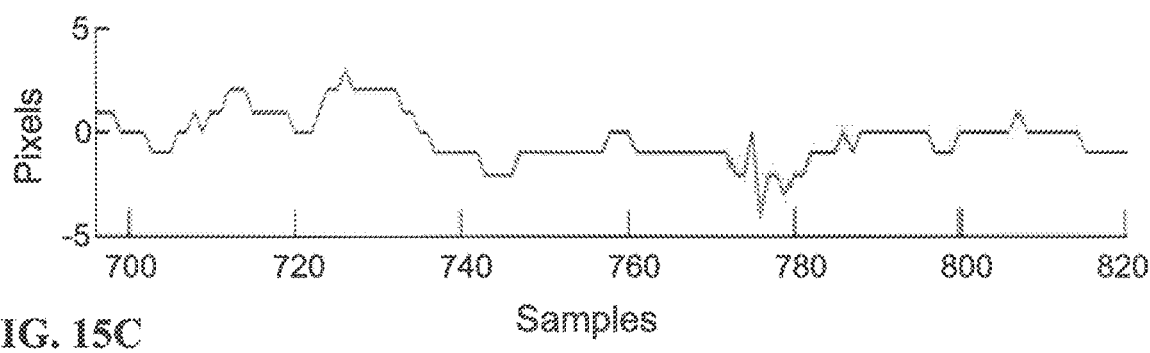
Figure 15C:
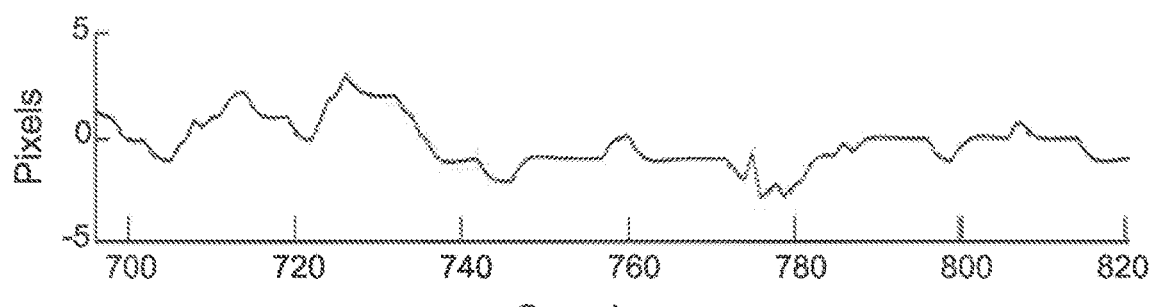
Figure 15D:
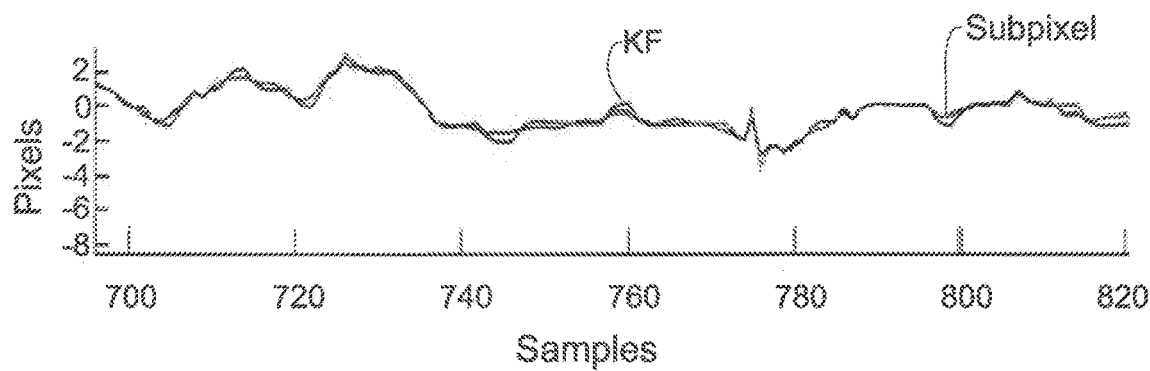
Figure 16A:
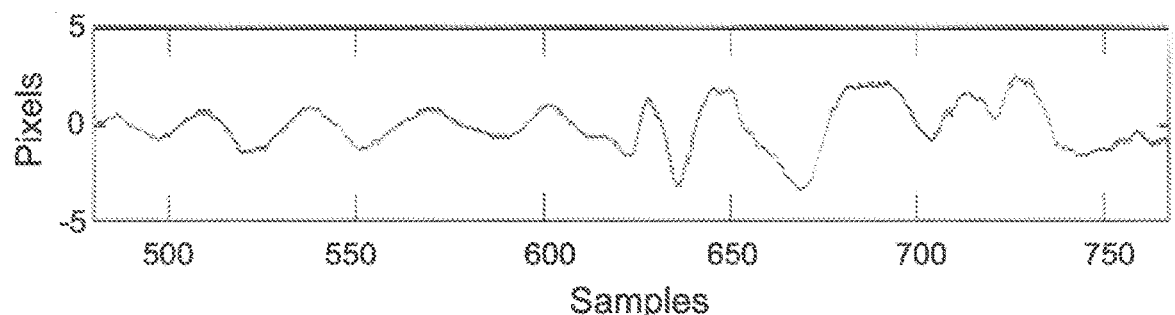
FIGS. 16A to 16D show reference, measured and estimated correlation data using nonlinear Kalman filtering, and comparison between reference and estimated correlation shifts respectively.
Figure 16B:
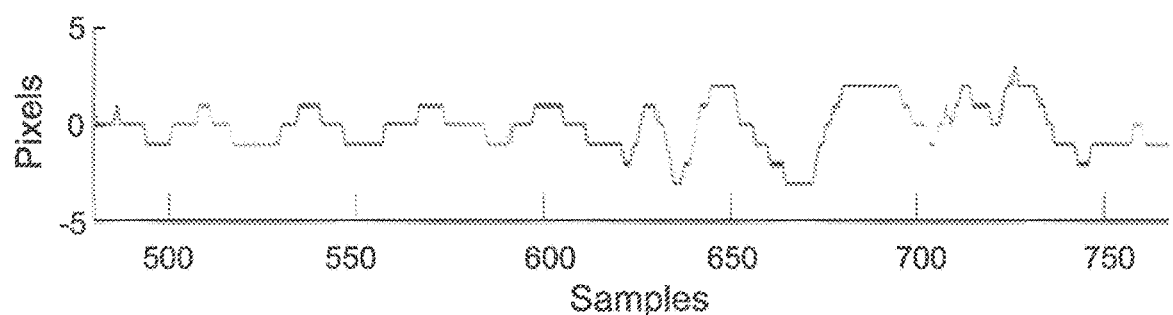
Figure 16C:
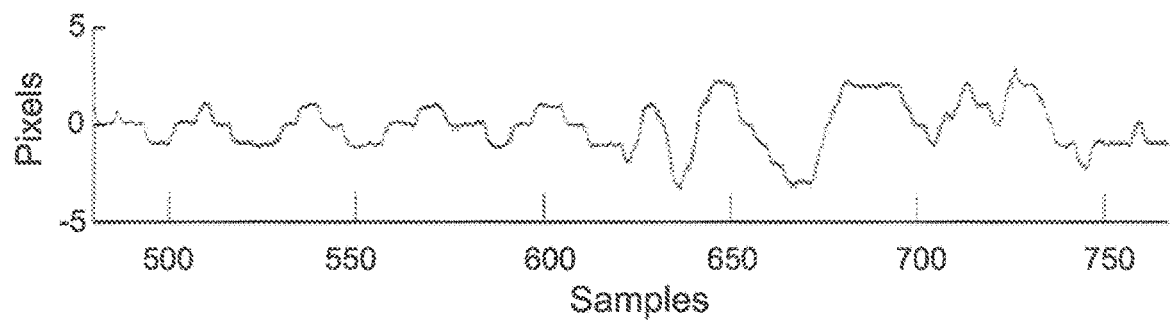
Figure 16D:
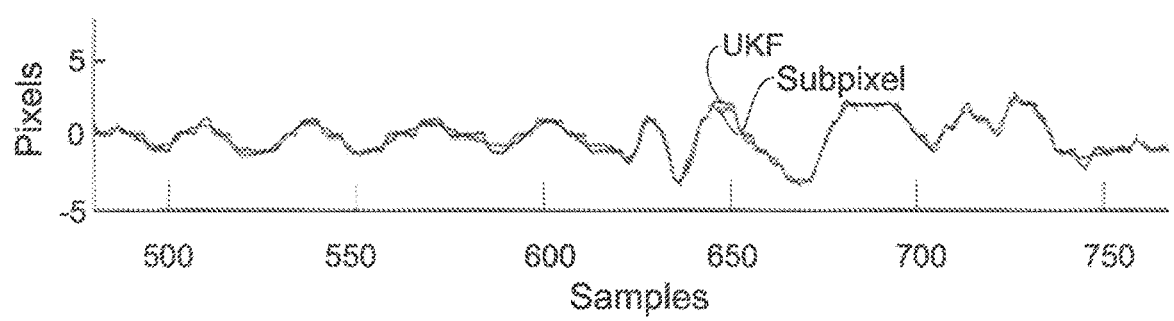

Reference is made to FIGS. 14A to 14C and 15A to 15D showing reference, measured and estimated correlation data using linear Kalman filtering as described above, and to FIGS. 16A to 16D showing corresponding correlation data using nonlinear Kalman filtering techniques. FIG. 14A shows sub-pixel reference correlation shift; FIG. 14B shows integer pixel measured correlation shift; and FIG. 14C shows estimated correlation shift using linear Kalman filtering. FIGS. 15A to 15C show enlarged images of the data of FIGS. 14A to 14C, and FIG. 15D shows the resemblance between the reference and the estimated correlation shift data. FIGS. 16A to 16D show reference correlation data (FIG. 16A), integer pixel measured correlation shift (FIG. 16B), estimated correlation shift (FIG. 16C) determined using non-linear Kalman filtering as described above, and comparison between the estimated and the reference correlation shift (FIG. 16D). A measure for accuracy and efficiency of the estimation may be provided by error energy, in the examples of linear Kalman filtering technique, the error energy of the integer correlation with respect to the reference is 247.63, and the error energy was reduced to 227.39 between the estimated correlation shift and the reference. In the non-linear example, the error energy reduced from 249.23 to 230.65 (error data provided by mean square error).

Figure 17A:
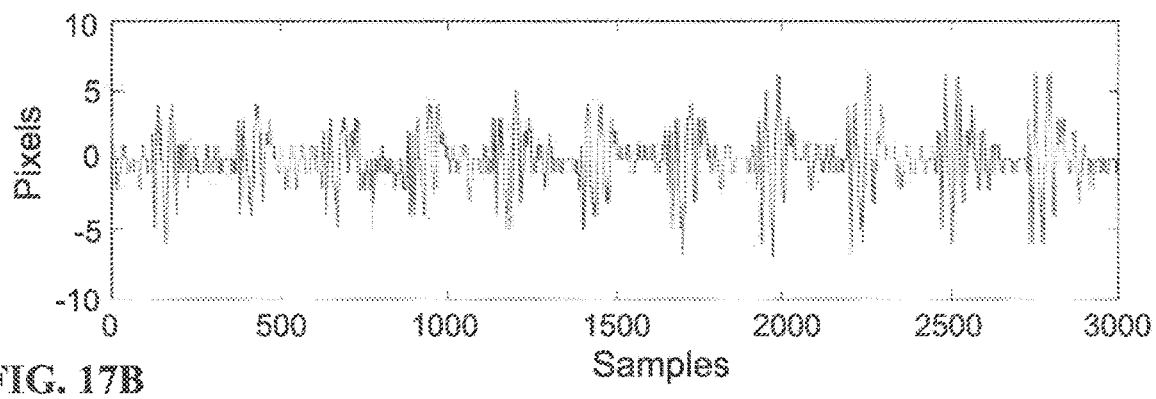
FIGS. 17A to 17C show integer correlation shifts determined based on collected image data pieces by collection sub-units having small (FIG. 17A), medium (FIG. 17B) and large (FIG. 17C) defocusing levels.
Figure 17B:
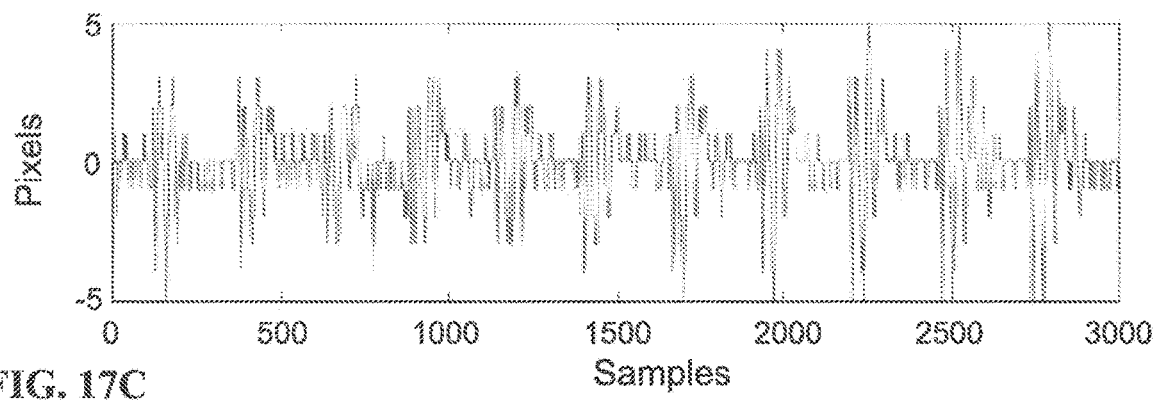
Figure 17C:
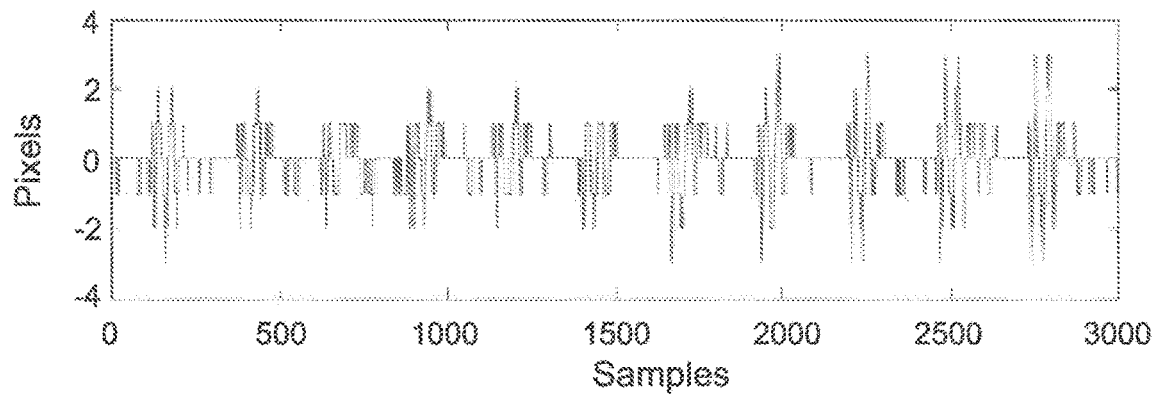
Figure 18A:
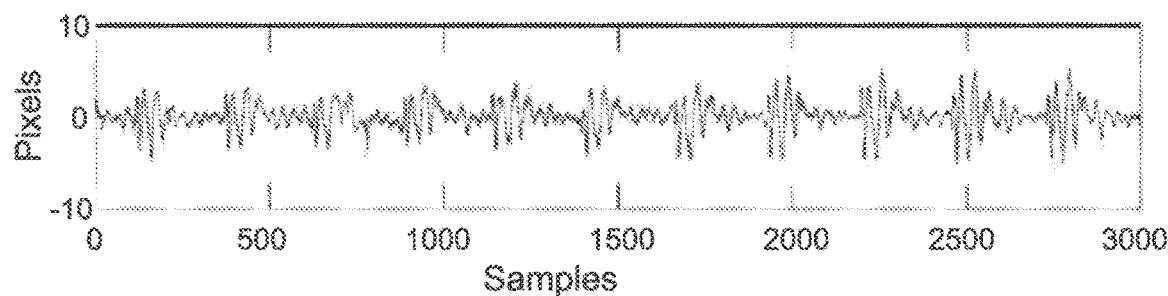
FIGS. 18A to 18D show sub-pixel reference correlation data (FIG. 18A), integer pixel measurement data of medium defocusing (FIG. 18B), estimated correlation shift using non-linear Kalman filtering based on the three-measurement series (FIG. 18C) and comparison to reference data (FIG. 18D)
Figure 18B:
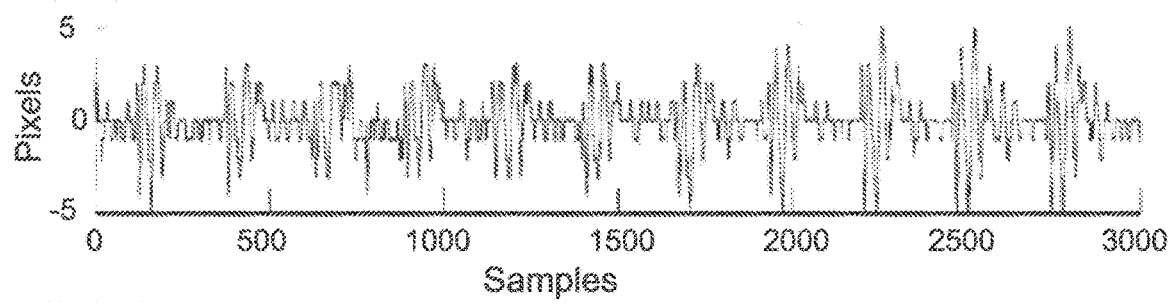
Figure 18C:
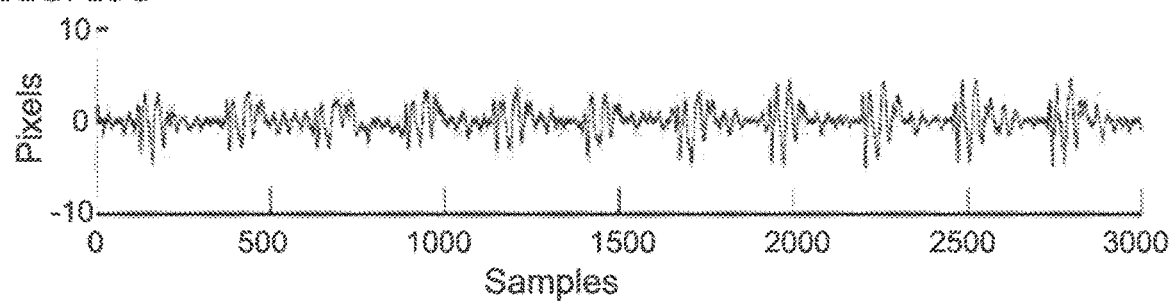
Figure 18D:
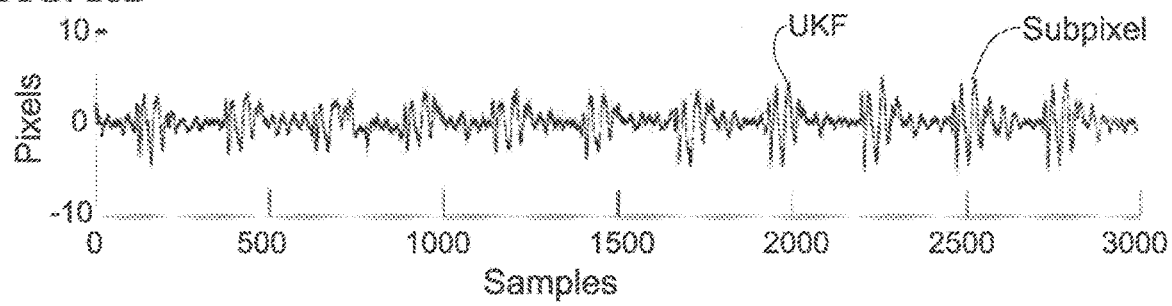
Figure 19A:
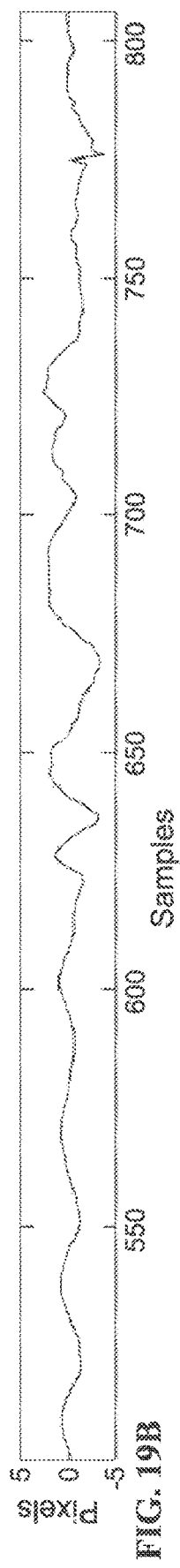
FIGS. 19A to 19D show enlarged section of the results of FIGS. 18A to 18D.
Figure 19B:
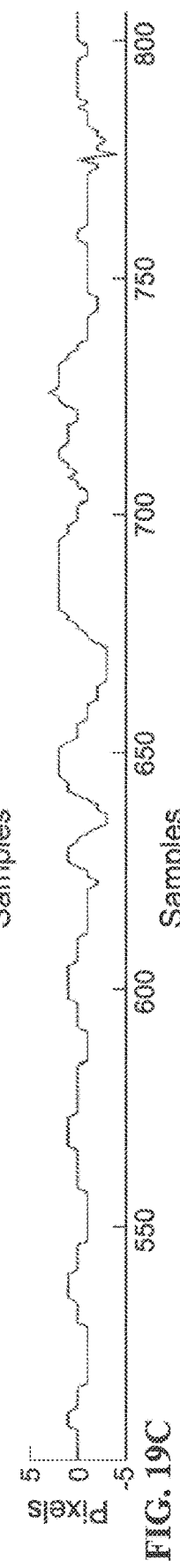
Figure 19C:
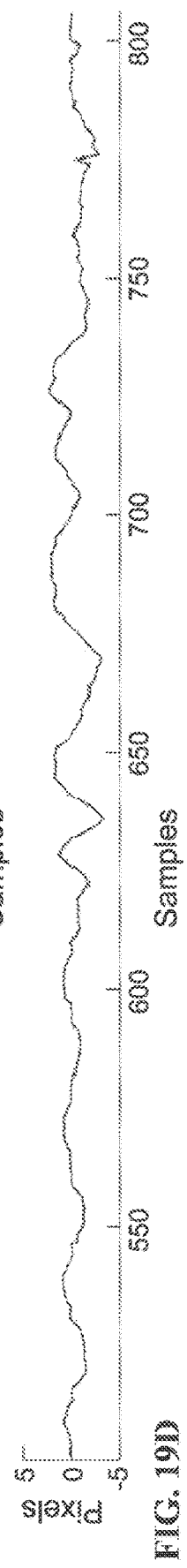
Figure 19D:
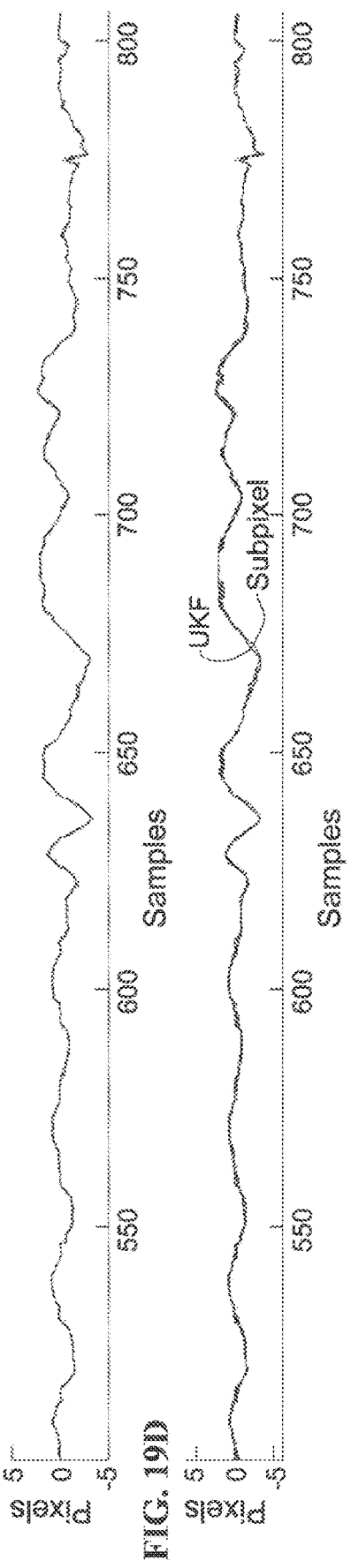

As indicated above, the estimated correlation shift may be improved using input measurement data from additional sources, i.e. using two or more collection sub-units as indicated above. Reference is made to FIGS. 17A to 17C showing integer correlation shifts determined based on collected image data pieces by collection sub-units having small (FIG. 17A), medium (FIG. 17B) and large (FIG. 17C) defocusing levels; to FIGS. 18A to 18D showing sub-pixel reference correlation data (FIG. 18A), integer pixel measurement data of medium defocusing (FIG. 18B), estimated correlation shift using non-linear Kalman filtering based on the three measurement series (FIG. 18C) and comparison to reference data (FIG. 18D); and to FIGS. 19A to 19D showing enlarged section of the results of FIGS. 18A to 18D. An error energy value of the integer correlation shift of FIGS. 17B and 18B with respect to the reference sub-pixel correlation is determined to be 247.63. the error energy for the estimated correlation shift of FIG. 18C with respect to the reference correlation is determined to be 158.16, showing high improvement in accuracy with respect to the estimation technique using single input source. Repeating similar technique on collected signal with relatively low signal to noise ratio showed further increase in accuracy and in proper estimation of the correlation shift.

Figure 20:
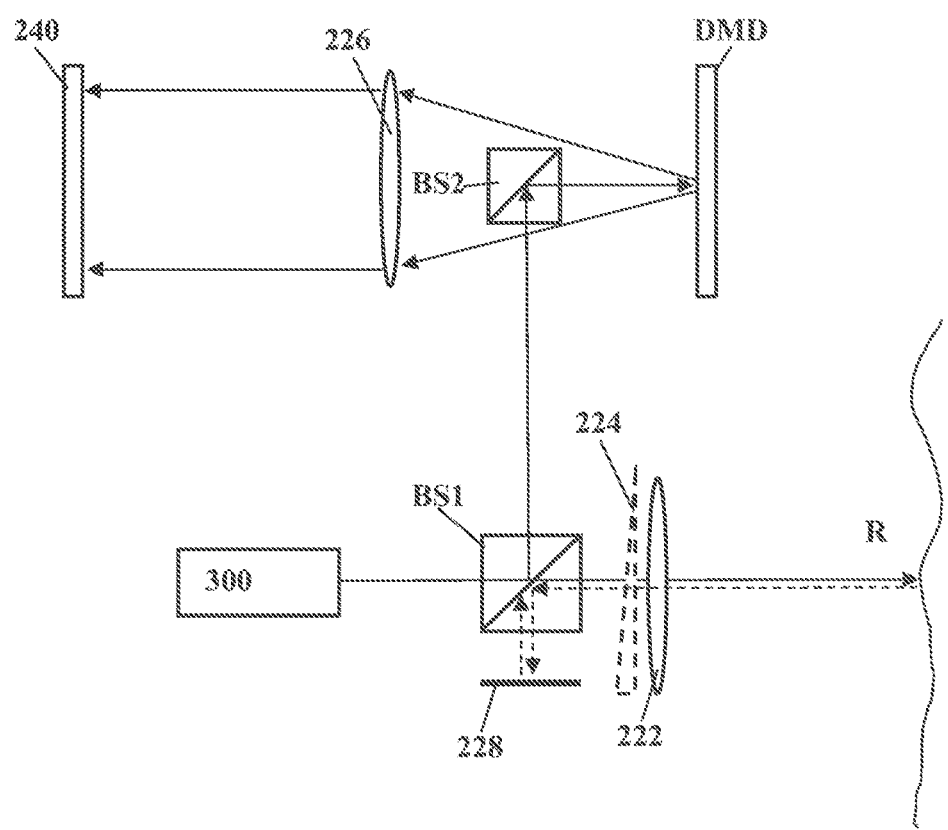
FIG. 20 illustrates an example of optical monitoring unit configured for determining correlation data using optical Fourier transform according to some embodiments of the invention.

Reference is made to FIG. 20 exemplifying an additional configuration for optical correlation. In this example, the technique utilizes optical Fourier transform of collected images reflected by (or transmitted through) digital micro-mirror device (DMD) configured to modulate light in accordance with previously collected image data. To this end, the DMD exemplified herein operates as a spatial light modulation unit where in the present example the modulation is achieved by variation in reflective properties. Generally, to provide real-space correlation function, the technique may further direct coherent light provided by a light source unit onto the DMD for obtaining second (inverse) optical Fourier transform indicative of correlation between the image data pieces.

As shown in FIG. 20, the collection system 200 includes optical arrangement configured for providing several optical paths for collection of light returning from the inspection region, as well as for illuminating the DMD unit. The optical arrangement includes first lens arrangement 222, light splitting unit BS1, reflecting element 228, and second lens arrangement 226 configured as Fourier lens arrangement. The optical arrangement may also include light deflecting unit 224 (e.g. prism) and second optical splitting unit BS2. The second lens arrangement 226 is configured as Fourier lens, providing optical Fourier transform between the DMD and the detector array 240, this is while defocusing is provided by combined optical operation of the first 222 and second 226 lens arrangements. It should be noted that the exemplary configuration illustrated in FIG. 20 utilizes DMD for modulation light by reflection. The present technique may utilizes transmission related light modulation technique such as spatial light modulation (SLM) unit where the light modulation is achieved by varying transmission of the light pattern rather than reflection thereof. Accordingly, the term DMD as used herein should be understood broadly and is directed to various types of spatial light modulation units as known in the art.

The exemplified configuration provides a joint transform correlator (JTC) using the DMD unit enabling to determine product of two images, and Fourier lens arrangement 226 for providing optical Fourier transform of the product of the two images. This technique enables determining spatial correlation using optical operation and thus omits the need of converting the collected image data to form a vector of numerical data piece (e.g. one-dimensional vector), which is typically required for computerized processing. Further, the rate of optical processing is typically limited by electronic interface thereto, e.g. transmission of data from the detector array to the DMD and readout of the detector array 240.

In this connection, optical spatial Fourier transform may typically be realized using one or more lenses appropriately positioned to provide Fourier transform relation between the optical field coming from the DMD and the field received at the detection plane of the detector array 240. Generally, initial two frames are being captured, using full reflecting arrangement of the DMD (or portion thereof). To this end optical illumination provided by the light source unit 300 is directed at the inspection region R and reflected light is collected through lens arrangement 222, transmitted to the DMD using BS1 and possibly BS2, and reflected from the DMD to be detected on detector array 240. A suitable image processing circuit (associated with circuit 500 in FIG. 1, not specifically shown in this figure) is configured for receiving image data pieces for two frames, and transmit corresponding data to the DMD, operating the DMD to provide reflection patterns corresponding to product of the two frames. When the DMD presents reflective patterns corresponding with product of the two frames, light from the light source is directed onto the DMD and provides Fourier transform image on the detector array 240 using Fourier lens arrangement 226. Typically, an additional Fourier transform is performed is the same technique to provide correlation data between the two frames.

To provide continuous monitoring, the optical arrangement of the collection unit may include light deflecting unit 224 (e.g. prism) configured for deflecting light returning from the inspection region to a parallel optical axis and use different portions of the detector array and the DMD for collecting image data from the inspection region. At the same time, other region of the detector array and DMD, or second detector and DMD are used for determining correlation between selected image data pieces collected at different times as described above. For example, the technique may be used for determining correlations between consecutive frames, or at different time differences depending on frame rate of operation.

Generally, the correlation in JTC configuration is realized in two temporal cycles. In the first cycle, the DMD is used to display two input frames (two speckle patterns that are to be correlated with each other) while the camera captures the intensity of the Fourier transform and then in the second temporal cycle the output of the camera is transmitted to be displayed on the DMD. In the second temporal cycle of display the correlation pattern data is typically collected on the detector array around the first order of diffraction (with respect to the optical Fourier transform). This technique is based on the relations between convolution and correlation operations as Fourier transform.

Figure 21A:
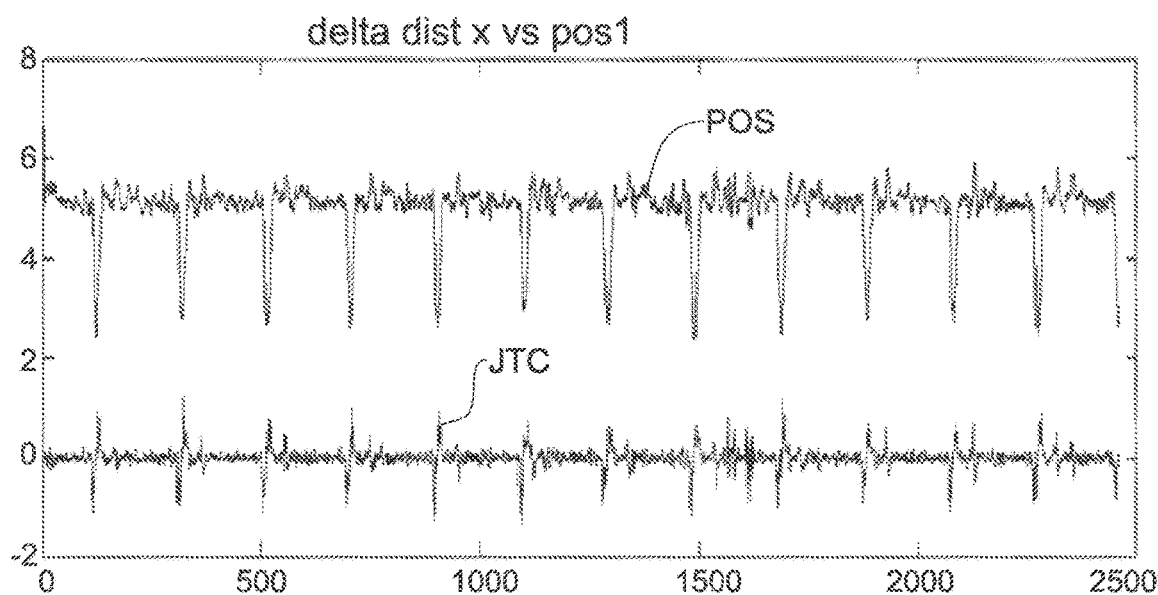
FIGS. 21A and 21B exemplify correlation shift data determined by convention computer processing and by optical Fourier transform.
Figure 21B:
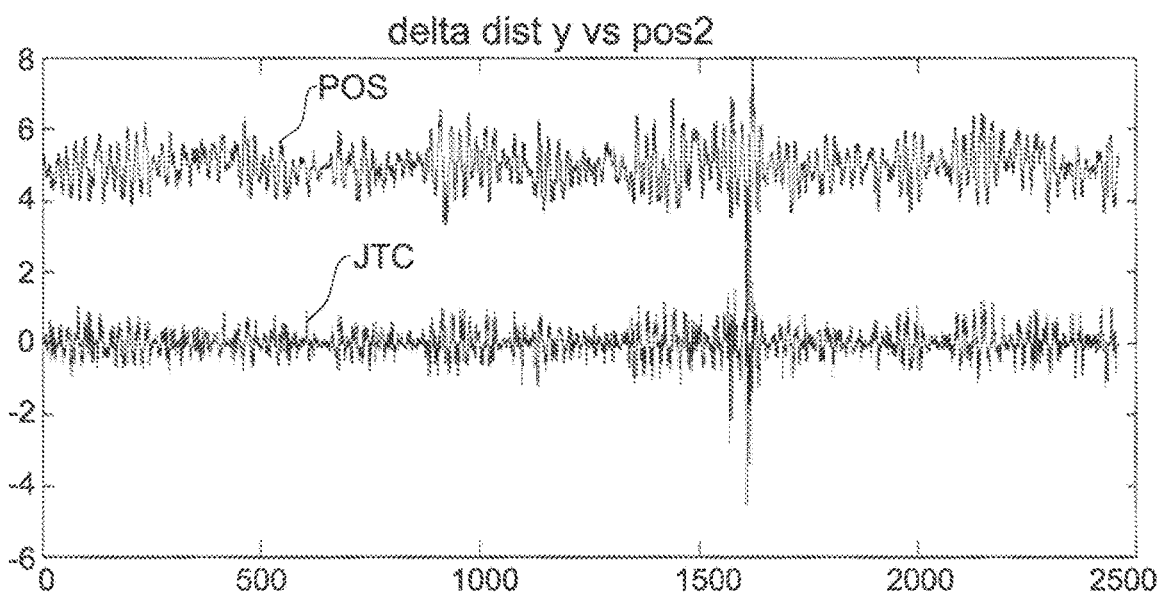

Reference is made to FIGS. 21A and 21B showing correlation shift data long x and y axes (with respect to image data plane) determined using conventional processing of image data pieces (POS) and correlation data determined by optical correlation as described herein (JTC). Certain variations between the correlation graphs can be seen, however for various proposes, such differences are generally reproducible and may thus may be considered when processing the correlation data to determine one or more parameters of the inspection region. Furthermore, the process of determining optical correlation data may require less processing power and time with respect to processing of the image data pieces for determining correlation along two axes.

Figure 22A:
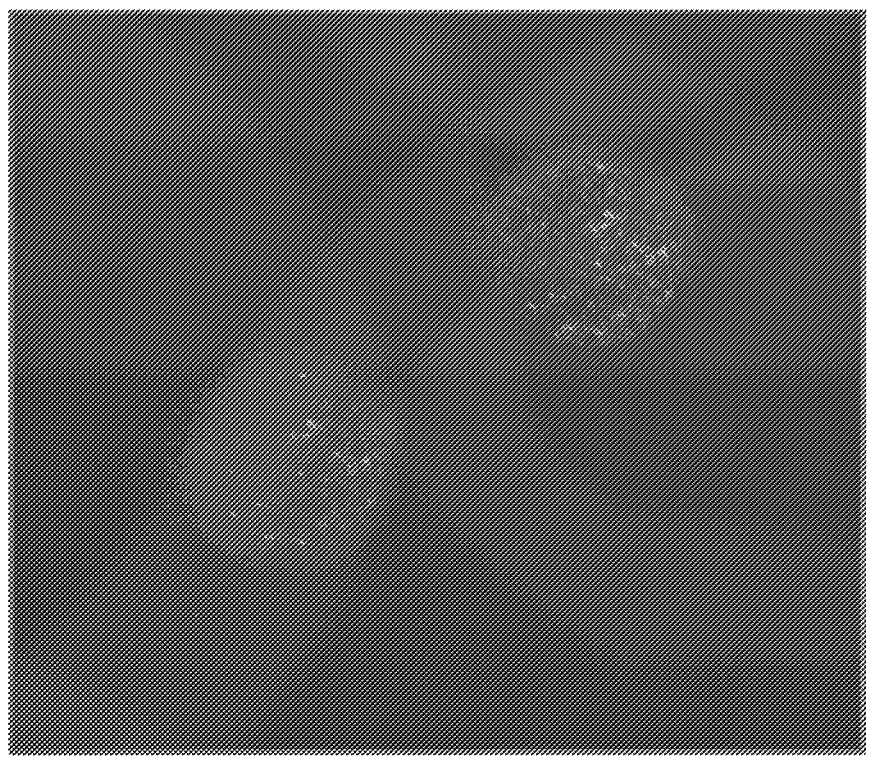
FIGS. 22A to 22D show collected image data associated with two frames, binary converted image data, optical Fourier transform of the collected image data, and inverse optical Fourier transform showing correlation between the two frames respectively.
Figure 22B:
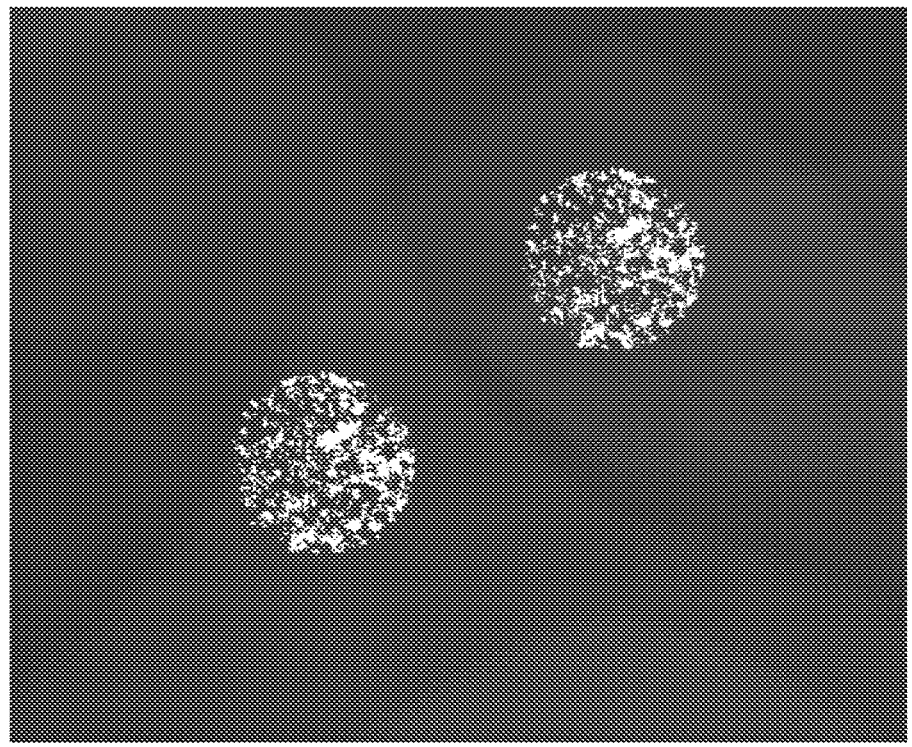
Figure 22C:
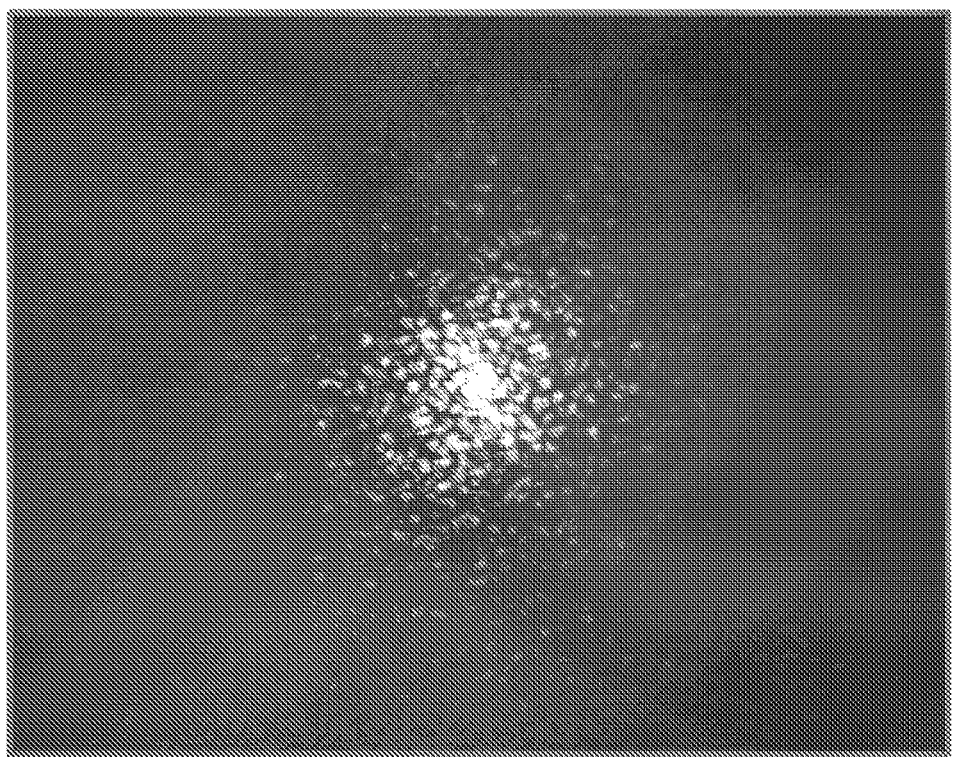
Figure 22D:
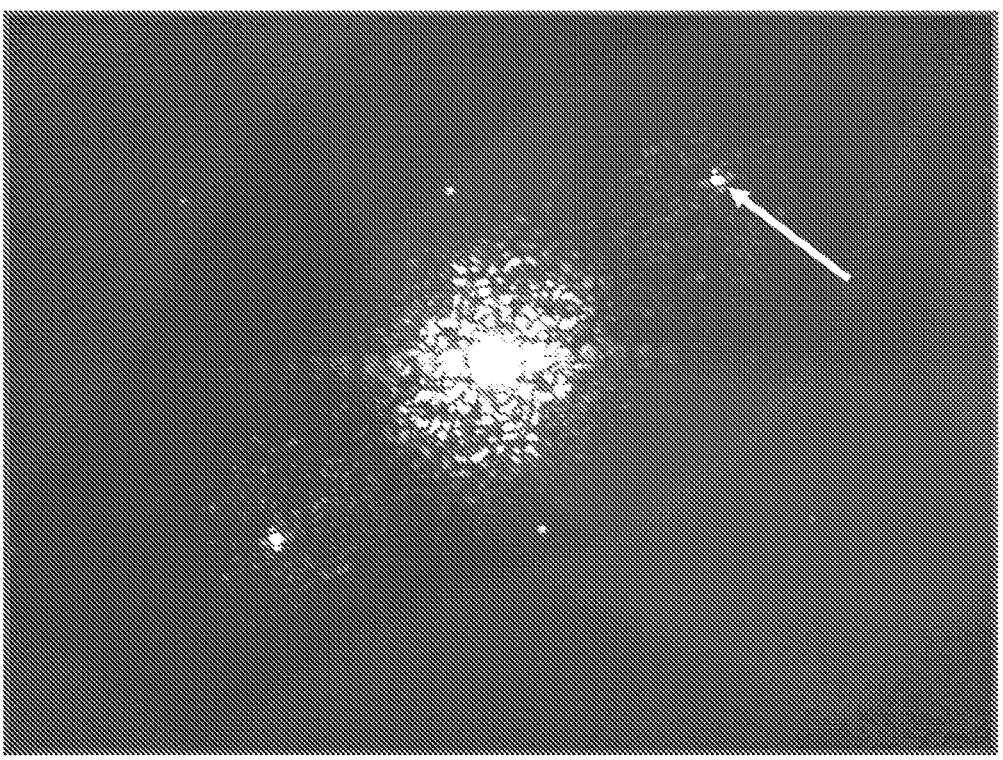

The process of Joint transform correlation (JTC) is exemplified in FIGS. 22A to 22D. FIG. 22A shows two image pieces corresponding to two frames of speckle patterns, in this case the frames are consecutively collected; FIG. 22B shows binary mapping image pieces suitable for light modulation by the DMD; FIG. 22C shows optical Fourier mapping of product of the two image pieces; and FIG. 22D shows inverse optical Fourier mapping indicative of convolution of the image pieces. Pick of correlation between the two image pieces is clearly seen in the image of FIG. 22D marked by arrow. The x-y location of the correlation pick is indicative of correlation shift data along x and y axes.

It should also be noted that an additional important added value associated with the use of optical correlation as described herein relates to the resolution of the correlation processing. Digitally computed correlation is typically limited by geometrical resolution of detection of the relevant image data pieces and may require sub pixel interpolation for the correlation to obtain sufficient resolution, i.e. avoid loss of resolution due with respect to resolution of the detector array. This is while optical processing is associated with manipulation of light propagation and thus no interpolation is needed to provide correlation data at the optimal resolution (determined by the detector array).

Accordingly, the present technique provides a system or unit for use in monitoring of an object. The system includes optical collection unit configured for collecting image data pieces from an inspection region at a selected sampling rate, and corresponding circuitry for one or more determining correlation functions between image data pieces collected at different times. The system may also include a coherent light source unit configured to provide coherent illumination of the inspection region. And the optical arrangement is aligned for defocused collection of images from the inspection region for forming image data indicative of secondary speckle pattern in the reflected/scattered light. The system of the invention may be configured as an add-on unit for use with additional electronic device or system having processing power, storage utility and user interface, for processing data indicative of the one or more correlation functions and determine accordingly one or more selected parameters/properties of the inspection region. The system of the invention may be used for monitoring biological properties of a patient (e.g. heart rate, breathing rate, pulse speed, glucose or alcohol concentrations etc.) and/or mechanical characteristics of any sample, being biological or not, typically combined with selected suitable external stimulation applied on the inspection region.

The invention claimed is:

1. A system for use in monitoring an object, the system comprising: a collection unit comprising at least one optical arrangement and at least one detector array arranged for defocused collection of light returning from a selected region on the object; and image data collection circuitry configured for receiving electronic signals associated with data piece collected by pixels of the at least one detector array and for generating output data indicative of correlation function between image frames collected by the detector array at two or more different temporal instances, wherein said detector array is operable as a rolling shutter detector; wherein said optical arrangement further comprises an image multiplying unit configured for duplicating collected images onto two or more regions of the detector array; and wherein said image data collection circuitry is associated with analog to digital conversion of output data based on combined data collected in said two or more regions of the detector array, thereby providing digital data associated with image data piece collected at two or more different temporal instances.

2. The system of claim 1, further comprising an illumination unit comprising at least one light source unit configured for providing coherent optical illumination onto the selected region on the object.

3. The system of claim 1, wherein said image data collection circuitry comprises analog data summation line configured for receiving analog collection data from said two or more regions of the detector array and provide summation data of said two or more region, an analog to digital conversion unit being operated for converting said summation data using two or more different conversion thresholds thereby providing output data indicative of correlation between said two or more regions of the detector array.

4. The system of claim 1, wherein said collection unit comprises a spatial light modulation unit configured for applying selected modulation to collected light along optical path between collection optics and the detector array, said image data collection circuitry is configured for receiving data indicative of collected image data pieces and for varying said spatial light modulation unit in accordance with the collected image data to thereby generate correlation between image data piece associated with two or more different temporal instances.

5. The system of claim 4, wherein said detector array is located on Fourier plane with respect to the spatial light modulation unit.

6. The system of claim 4, wherein said optical arrangement comprises a light deflection unit configured for deflecting path of collected light thereby enabling simultaneous collection of defocused image data indicative of the inspection region and Fourier image data associated with light modulation by the spatial light modulation unit.

7. The system of claim 4, wherein said optical arrangement is configured for directing collected light forming at least two copies of the collected light such that one copy of the collected light is directed at the detector array for collecting image data pieces to thereby enable modulation of the spatial light modulation unit accordingly, and one other copy of collected light is directed at the spatial light modulation unit for interacting with modulation pattern thereof to provide correlation between previously collected image data.

8. The system of claim 4, wherein said spatial light modulation unit is a digital mirror device (DMD).

9. The system of claim 1, wherein said collection unit comprises two or more optical arrangements and corresponding two or more detector arrays arranged with different defocusing levels with respect to the selected region on the object, and wherein said image data collection circuitry comprises two or more digital signal processors associated with said two or more detector array and configured for determining variation in collected image data pieces, and an averaging unit configured for receiving input data from said two or more digital signal processors and determining an average variation in collected image data pieces being indicative of correlation function between image data pieces associated with two or more different temporal instances.

10. The system of claim 9, wherein said averaging unit of the image data collection circuitry is configured for determining a weighted average variation associated with correlation function between image data pieces in accordance with pre-stored steering vector corresponding to variations in levels of defocusing between said two or more optical arrangement and the corresponding detector arrays.

11. The system of claim 10, wherein said averaging unit is configured for using fixed weights for determined said weighted average in accordance with said steering vector.

12. The system of claim 10, wherein said averaging unit is configured for using adaptive weights for determining said weighted average in accordance with said steering vector.

13. The system of claim 12, wherein said adaptive weights are determined in accordance with estimated value of variation in collected image data pieces of said two or more detector arrays.

14. The system of claim 12, wherein said adaptive weights are determined using signal power covariance estimation associated with variation in collected image data pieces of said two or more detector arrays.

15. The system of claim 9, wherein said averaging unit of the image data collection circuitry is configured for determining an optimal estimation of said correlation function by linear or non-linear Kalman filtering technique.

16. A method for use in monitoring properties of an object, the method comprising: collecting light returning from a region of the object using defocused optical arrangement and generating at least two defocused image regions onto a detector array; using a rolling shutter readout mode of the detector array and generating at least two temporally shifted image readout pieces associated with said at least two defocused image regions; summing said at least two temporally shifted image readout pieces providing a combined readout data vector; applying analog to digital conversion using two or more different threshold levels and determining difference vector between said two or more conversions, thereby providing data indicative of spatial correlation between said at least two defocused image regions.

17. A system for use in monitoring an object, the system comprising: a collection unit arranged for defocused collection of light returning from a selected region on the object and comprising at least one rolling shutter detector array and an optical arrangement, the optical arrangement comprises an image multiplying unit configured for duplicating collected images onto two or more regions of the detector array; and image data collection circuitry configured comprising analog to digital conversion module, said image data collection circuitry is configured for receiving analog electronic signals associated with data piece collected by pixels of the two or more regions of the detector array and for generating output digital associated with conversion of combined data collected in said two or more regions of the detector array.

18. The system of claim 17, wherein said image data collection circuitry comprises analog data addition line configured for receiving analog collection data from said two or more regions of the detector array and provide summation data of said two or more region, said analog to digital conversion module being operated for converting said summation data using two or more different conversion thresholds thereby providing output data indicative of correlation between said two or more regions of the detector array.

\* \* \* \* \*